US009585633B2

(12) United States Patent
Gao et al.

(10) Patent No.: US 9,585,633 B2
(45) Date of Patent: Mar. 7, 2017

(54) METHODS AND APPARATUSES FOR MONITORING GASTROESOPHAGEAL REFLUX VOLUME WITH ULTRASONIC CATHETER

(75) Inventors: Xuexin Gao, Calgary (CA); Daniel C. Sadowski, Edmonton (CA); Martin P. Mintchev, Calgary (CA)

(73) Assignee: UTI LIMITED PARTNERSHIP, Calgary (CA)

( * ) Notice: Subject to any disclaimer, the term of this patent is extended or adjusted under 35 U.S.C. 154(b) by 913 days.

(21) Appl. No.: 13/222,556

(22) Filed: Aug. 31, 2011

(65) Prior Publication Data

US 2012/0078074 A1    Mar. 29, 2012

Related U.S. Application Data

(60) Provisional application No. 61/378,701, filed on Aug. 31, 2010.

(51) Int. Cl.
| | | |
|---|---|---|
| *A61B 8/12* | (2006.01) | |
| *A61B 5/05* | (2006.01) | |
| *A61B 8/08* | (2006.01) | |
| *A61B 5/053* | (2006.01) | |
| *A61B 5/145* | (2006.01) | |
| *A61B 5/00* | (2006.01) | |

(52) U.S. Cl.
CPC ............. *A61B 8/12* (2013.01); *A61B 8/5223* (2013.01); *A61B 5/0538* (2013.01); *A61B 5/14539* (2013.01); *A61B 5/4211* (2013.01)

(58) Field of Classification Search
CPC ............. A61B 8/12; A61B 5/06; A61B 8/4254
USPC .................................... 600/350, 466
See application file for complete search history.

(56) References Cited

U.S. PATENT DOCUMENTS

| | | | |
|---|---|---|---|
| 4,119,498 A | 10/1978 | Edwall et al. ................. | 205/782 |
| 4,417,583 A | 11/1983 | Bechai et al. ................. | 600/463 |
| 4,802,490 A | 2/1989 | Johnston ........................ | 600/454 |
| 5,247,938 A | 9/1993 | Silverstein et al. ........... | 600/459 |
| 5,479,928 A | 1/1996 | Cathignol et al. ............. | 600/454 |
| 5,524,622 A | 6/1996 | Wilson .......................... | 600/431 |
| 5,833,625 A | 11/1998 | Essen-Moller ................ | 600/547 |
| 6,398,734 B1 | 6/2002 | Cimochowski et al. ..... | 600/454 |
| 2003/0013958 A1* | 1/2003 | Govari et al. ................ | 600/437 |
| 2005/0182342 A1 | 8/2005 | Dinsmoor et al. ........... | 600/593 |
| 2006/0122514 A1* | 6/2006 | Byrd et al. ................... | 600/466 |
| 2007/0043290 A1* | 2/2007 | Goepp et al. ................. | 600/437 |
| 2008/0004547 A1 | 1/2008 | Dinsmoor et al. ........... | 600/593 |
| 2008/0097150 A1* | 4/2008 | Hasegawa et al. ........... | 600/109 |
| 2008/0119727 A1* | 5/2008 | Barbagli et al. .............. | 600/424 |

OTHER PUBLICATIONS

Barlow and Orlando, "The pathogenesis of heartburn in nonerosive reflux disease: a unifying hypothesis," *Gastroenterology*, 128(3): 771-778, 2005.

(Continued)

*Primary Examiner* — Patricia Mallari
*Assistant Examiner* — Michael Catina
(74) *Attorney, Agent, or Firm* — Norton Rose Fulbright US LLP

(57) ABSTRACT

Ultrasonic catheters and methods for determining and/or monitoring reflux volumes during gastroesophageal reflux events.

9 Claims, 11 Drawing Sheets

(56) References Cited

OTHER PUBLICATIONS

Gao et al., "Intraluminal ultrasonic probe for volumetric monitoring of liquid gastroesophageal reflux," *Physiol. Meas.*, 33:487-501, 2012.
Gao et al., "Pilot study of longitudinal ultrasonic sensor for dynamic volumetric assessment of gastroesophageal reflux," *Conf Proc IEEE Eng Med Biol Soc*, 2010:899-902, 2010.
GI Motility Online, "Physiology of esophageal motility". [Online]. Available: http://www.nature.com/gimo/contents/pt1/full/gimo3.html [Mar. 20, 2010].
Gonzalez et al., "Gastroesophageal scintigraphy: a useful screening test for GE reflux," *J Pediatr Gastroenterol Nutr.*, 6(2): 217-219, 1987.
Gwendolyn et al., "Chapter 18. Respiratory Tract & Mediastinum," *Current Diagnosis & Treatment: Pediatrics*, 9th ed., W. Hay, Jr., M. Levin, J. Sondheimer and R. Deterding. [Online]. Available: http://www.accessmedicine.com/content.aspx?aID=3402130. [Nov. 2, 2009].
Hedrick, *Ultrasound physics and instrumentation*, St. Louis, MO: Elsevier Mosby, p. 1-82, 2005.
Imam et al., "Bolus transit patterns in healthy subjects: a study using simultaneous impedance monitoring, videoesophagram, and esophageal manometry," *Am. J Physiol. Gastrointest Liver Physiol.*, 288(5): G1000-G1006, 2005.
Klauser et al., "Symptoms in gastro-oesophageal reflux disease," *Lancet*, 335(8683):205-208, 1990.
Kuttruff *Acoustic An introduction*. New York, NY: Taylor & Francis, 2007, pp. 258-282, 345-348.
Lazarescu and Sifrim, "Ambulatory monitoring of GERD: current technology," *Gastroenterol Clin North Am.*, 37(4): 793-805, 2008.
Manoli et al., "Estimation of ventricular volume with an intracardiac ultrasonic catheter," *Pflgers Arch.*, 349:369-376, 1974.
Mittal et al., "Sensory and motor function of the esophagus: lessons from ultrasound imaging," *Gastroenterology*, 128(2): 487-497, 2005.
Orenstein et al., "Thickening of infant feedings for therapy of gastroesophageal reflux," *J. Pediatr.*, 110(2): 181-186, 1987.
Pandolfino et al., "Esophagogastric junction opening during relaxation distinguishes nonhernia reflux patients, hernia patients, and normal subjects," *Gastroenterology*, 125:1018-1024, 2003.
Patti and Fisichella, "Chapter 20. Esophagus & Diaphragm," in Current Diagnosis & Treatment: Surgery, 13th ed., Doherty GM. [Online]. Available: http://www.accessmedicine.com/content.aspx?aID=5215311, Oct. 6, 2009.
Sellar et al., "Barium radiology: a sensitive test for gastro-oesophageal reflux," *Clin Radiol.*, 38(3): 303-307, 1987.
Shaheen and Ransohoff. "Gastroesophageal reflux, barren esophagus and esophageal cancer: scientific review," *JAMA*, 287(15): 1972-1981, 2002.
Sifrim et al., "Review article: acidity and volume of the refluxate in the genesis of gastro-oesophageal reflux disease symptoms," *Aliment Pharmacol Ther.*, 25(9): 1003-1017, 2007.
Sifrim. "Relevance of volume and proximal extent of reflux in gastro-oesophageal reflux disease." *Gut*, 54:175-178, 2005.
Silny, "Intraluminal multiple electrical impedance procedure for measurement of gastrointestinal motility," *Neurogastroenterology & Motility*, 3:151-162, 1991.
Simren et al., "Relevance of ineffective oesophageal motility during oesophageal acid clearance.," *Gut*, 52: 784-790, 2003.
Spechler. "Clinical practice. Barrett's Esophagus," *N Engl J Med.*, 346(11): 836-842, 2002.
Srinivasan et al., "Esophageal function testing using multichannel intraluminal impedance." *Am J Physiol Gastrointest Liver Physiol.*, 280:G457-462, 2001.
Tipnis et al., "Common cavity pressure during gastroesophageal reflux: reassessment using simultaneous pressure, impedance, and ultrasound imaging," *Am J Physiol Gastrointest Liver Physiol*, 290:1149-1156, 2006.
United State National Institute of Health, "Digestive disease statistics". [Online] Available: http://digestive.niddk.nih.gov/statistics/statistics.htm, Oct. 1, 2009.
Yang et al., "Finite element simulation of food transport through the esophageal body," *World J Gastroenterol.*, 13:1352-1359, 2007.
Yorozu et al., "Common cavity pressure during gastroesophageal reflux: reassessment using simultaneous pressure, impedance, and ultrasound imaging," *Am J Physiol Gastrointest Liver Physiol.*, 290(6): G1149-1156, 2006.

\* cited by examiner

METHODS AND APPARATUSES FOR MONITORING GASTROESOPHAGEAL REFLUX VOLUME WITH ULTRASONIC CATHETER

CROSS-REFERENCE TO RELATED APPLICATIONS

This application claims priority to U.S. Provisional Patent Application No. 61/378,701, filed Aug. 31, 2010, the entire contents of which are incorporated by reference.

BACKGROUND

1. Field of the Invention

The present invention relates generally to intraluminal ultrasonic measurement, and, more particularly, but not by way of limitation, to devices and methods for measuring reflux volume during spontaneous gastroesophogeal reflux (GER) events.

2. Description of Related Art

Recent statistics provided by the National Institutes of Health, suggest that symptoms consistent with Gastroesophageal Reflux Disease (GERD) resulted in 710,000 hospitalizations in the USA for 2002 [1]. GERD is generally caused by abnormal retrograde flow of gastric content into the esophagus, and may result in various symptoms such as mucosal damage [2]. GERD is one of the most common conditions that affect the gastrointestinal tract, and is usually thought to be the cause of many esophageal symptoms [10]. Individuals suffering from GERD may experience symptoms such as heartburn or a substernal burning sensation in the chest [3]. In addition, untreated GERD may lead to further consequences, such as esophagitis and Barrett's esophagus, which has been considered a precursor to esophageal cancer [4, 5].

Various techniques have been devised to diagnose GERD, but methods for quantifying the volume of a spontaneous reflux event are currently lacking [11]. Presently, three techniques have been attempted to monitor the volume of reflux, namely, (a) video-fluoroscopy; (b) combined ambulatory multichannel impedance-pH monitoring and (c) high-frequency intraluminal ultrasonic methods [11].

Video-fluoroscopy is an imaging technique using X-rays to obtain real-time dynamic video of the internal organs of a patient. This technique may be indicated for patients with suspected aspiration, to detect swallowing dysfunction, gastroesophageal reflux, and achalasia [15]. While anatomic and functional information related to GERD might be provided by this stationary method, non-physiological conditions are required to induce gastroesophageal reflux phenomena during testing [11-14]. In addition, fluoroscopy usually involves exposure of the subject to significant amounts of ionizing radiation, which limits the duration of the test and practical feasibility for detecting spontaneous reflux events. Thus, video-fluoroscopy and other similar radiology methods (e.g. esophageal scintigraphy [12]) are generally not suitable for monitoring spontaneous reflux episodes.

Multichannel impedance-pH monitoring has been developed for gastroesophageal reflux detection [6, 14, 16-18]. As explained by Lazarescu and Silny [14, 16], this technique is generally based on measuring electrical impedance between electrodes mounted on a thin intraluminal catheter. If the electrodes are in contact with content of high ionic concentration, e.g., swallowed or refluxed material, low impedance is measured. Correspondingly, if they are in contact with content of low ionic concentration, e.g., air or esophageal lining, high impedance is measured. Also, impedance changes in the temporal-spatial patterns at different positions on the catheter within the esophagus facilitate the differentiation between antegrade and retrograde bolus movement. U.S. Pat. No. 5,833,625, entitled Ambulatory Reflux Monitoring System, describes a system for monitoring reflux based on impedance changes in the esophagus. U.S. Pat. No. 4,119,498, entitled Monocrystalline Metal Electrode and Method of Use, describes a metal electrode for determining pH.

Multichannel impedance-pH monitoring may have a high sensitivity in detecting the proximal extent of reflux and the duration of acid clearance [6, 14]. However, the correlation between the volume and the proximal extent of the reflux may be adversely affected by several specific factors, such as specific characteristics of the refluxed gastric content, the compliance of the gastroesophageal junction, and the gastroesophageal pressure gradient [6, 19-20]. Additionally, as described by Srinivasan [21], similar decreases in impedance system output were observed when different volumes of liquid boluses were swallowed by the same subject.

U.S. Pat. No. 6,398,734, entitled Ultrasonic Sensors for Monitoring the Condition of Flow through a Cardiac Valve, discloses a band with two ultrasonic transducers to be wrapped around a cardiac vessel in order to evaluate the shape of the vessel and the velocity of the blood flow in the vessel. U.S. Pat. No. 5,247,938, entitled Method and Apparatus for Determining the Motility of a Region in the Human Body, describes an apparatus using ultrasonic probes for monitoring the movement of the digestive tract wall. This objective was accomplished by attaching several ultrasonic probes to a region of the intestinal wall and processing the echo signals. The systems disclosed in these two patents are not catheter-based, and generally require complicated and/or invasive setup operation procedures.

U.S. Pat. No. 4,802,490, entitled Catheter for Performing Volumetric Flow Rate Determination in Intravascular Conduits, presents an apparatus for determining volumetric information of vascular conduit using an intraluminal catheter. A transverse ultrasonic transducer and an inflatable balloon are positioned on the distal portion of the catheter. The ultrasonic signal is connected and processed by a Doppler circuit to record blood velocity both when the balloon is inflated and deflated. Thereafter, the internal cross-sectional area of the blood vessel is calculated based on the assumption that the cardiac output is constant regardless whether the balloon is inflated or not. However, this assumption is not adequate for measuring the volume of reflux which changes temporally and frequently.

Intraluminal ultrasonic imaging catheters have been used to measure the cross-sectional area of the distal esophagus during distensions by bolus swallows or spontaneous reflux events [6, 14]. Compared to distal distension in normal subjects, larger distensions of the esophagus were found in patients with GERD symptoms [7], [8]. An example of such ultrasonic methods is described in U.S. Pat. No. 4,417,583, entitled Apparatus and Method of Internal Examination of Gastrointestinal Tract and Adjacent Organs, which presents an ultrasonic imaging method for examining an organ of the gastrointestinal tract. Current intraluminal ultrasonic imaging systems are generally limited to stationary studies and require complicated test procedures. Moreover, due to their use of cumbersome image processing, these systems are not appropriate for 24-hour ambulatory monitoring or detecting spontaneous reflux events [8].

SUMMARY

This disclosure includes embodiments of methods and apparatuses (and/or systems) for measuring and/or monitoring reflux volume during gastroesophageal reflux events.

In patients with GERD, esophageal symptoms generally relate to increased contact time between the gastric content and the esophagus. Although known methods of investigating GER events generally do not provide satisfactory ways of quantifying reflux volume, the volume of the refluxate may be important to better understand the pathophysiology of GERD [6]. By estimating the reflux volume, both the prolonged time of distal mucosal exposure to the refluxates and the total amount of highly concentrated damaging substances can be quantified. Therefore, the present methods of determining and/or monitoring reflux volume will help to better understand damaging phenomena of GERD and to evaluate the efficacy of antireflux treatment [6, 14]. To accurately measure the volume of reflux in the esophagus, it may generally be important to measure the geometric characteristics of the esophageal lumen during reflux. Embodiments of the present ultrasonic catheters can be coupled to a suitably configured controller or data acquisition system to monitor the dynamics of gastroesophageal reflux volume. Embodiments of the present ultrasonic catheters can be configured to provide a small and/or low-cost diagnostic tool for gastroesophageal reflux volume monitoring in 24-hour ambulatory studies (e.g., in which the patients could continue with their typical daily activities).

Some embodiments of the present apparatuses comprise: a catheter having a distal end; an ultrasonic transducer coupled to the distal end of the catheter; and a controller configured to be coupled to the catheter such that the controller can receive ultrasonic signals (e.g., echo signals) from the ultrasonic transducer, the controller further configured to determine from the ultrasonic signals an indication of reflux volume during a gastroesophageal reflux (GER) event of a patient.

Some embodiments of the present apparatuses comprise: a catheter having a distal end (e.g., and a peripheral surface); an ultrasonic transducer coupled to the distal end of the catheter; and a plurality of electrodes coupled in spaced relation along a length of (e.g., the peripheral surface of) the catheter; where the catheter is configured to be coupled to a controller such that the controller can receive impedance signals from the plurality of electrodes and ultrasonic signals from the ultrasonic transducer. Some embodiments of the present apparatuses further comprise: a controller configured to be coupled to the catheter such that the controller can receive ultrasonic signals from the ultrasonic transducer, the controller further configured to determine from the ultrasonic signals an indication of reflux volume during a gastroesophageal reflux event of a patient.

In some embodiments of the present apparatuses, the transducer is configured to emit ultrasonic signals at a frequency at or above 1 MHz.

In some embodiments of the present apparatuses, the catheter is configured to be disposed within an esophagus of a patient such that the transducer is disposed at or a distance above the patient's lower esophageal sphincter (LES), and the controller is configured to determine a radius of the esophagus based on an echo peak in the ultrasonic signals received from the transducer.

In some embodiments of the present apparatuses, the controller is configured to determine a radius of the esophagus based on the elapsed time of echo peaks in the ultrasonic signals received from the transducer. In some embodiments, the controller is configured to determine an indication of reflux volume during a GER event by modeling at least a portion of the esophagus (e.g., between the transducer and the patient's LES) as a cylinder with the determined radius.

In some embodiments of the present apparatuses, the controller is configured to filter at least one of the signals received from the ultrasonic transducer, and the indications of reflux volume determined, to remove events having a duration below a threshold duration. In some embodiments, the threshold duration is greater than 2 seconds. In some embodiments, the threshold duration is greater than 5 seconds.

In some embodiments of the present apparatuses, the controller is configured to rectify the signal received from the ultrasonic transducer.

In some embodiments of the present apparatuses, the controller is configured to identify reflux events based on reductions in amplitude of the signal received from the ultrasonic transducer.

Some embodiments of the present methods comprise: receiving ultrasonic signals from an ultrasonic transducer disposed within a patient's esophagus a distance above the patient's lower esophageal sphincter (LES); and determining from the ultrasonic signals an indication of reflux volume during a gastroesophageal reflux event of the patient.

In some embodiments of the present methods, the ultrasonic transducer is a longitudinal ultrasonic transducer.

In some embodiments of the present methods, determining an indication of reflux volume comprises: disposing a catheter having an ultrasonic transducer in the esophagus of a patient such that the transducer is disposed at or a distance above the patient's lower esophageal sphincter (LES). In some embodiments, determining an indication of reflux volume further comprises: determining a radius of the esophagus based on an echo peak in the ultrasonic signals received from the transducer. In some embodiments, determining a radius includes determining the radius based on the elapsed time of echo peaks in the ultrasonic signals received from the transducer.

Some embodiments of the present methods further comprise: determining an indication of reflux volume during a GER event by modeling at least a portion of the esophagus as a cylinder with the determined radius.

Some embodiments of the present methods further comprise: filtering the signals received from the ultrasonic transducer to remove events having a duration below a threshold duration. In some embodiments, the threshold duration is greater than 2 seconds. In some embodiments, the threshold duration is greater than 5 seconds.

Some embodiments of the present methods further comprise; rectifying the signal received from the ultrasonic transducer.

Some embodiments of the present methods further comprise: identifying one or more reflux events based on one or more reductions in amplitude of the signal received from the ultrasonic transducer.

Some embodiments of the present apparatuses comprise: a catheter having a distal end (e.g., and a peripheral surface); a spaced longitudinal ultrasonic transducer pair coupled to (e.g., the peripheral surface of) the catheter; where the catheter is configured to be coupled to a controller such that the controller can receive ultrasonic signals from the longitudinal ultrasonic transducer pair. Some embodiments further comprise: a controller configured to be coupled to the catheter such that the controller can receive signals from the longitudinal ultrasonic transducer pair, the controller further configured to determine from the ultrasonic signals an indication of reflux volume during a gastroesophageal reflux event of a patient.

Some embodiments of the present apparatuses further comprise: a plurality of electrodes coupled in spaced relation along a length of (e.g., the peripheral surface of) the catheter; where the catheter is configured to be coupled to a controller such that the controller can receive impedance signals from the plurality of electrodes.

Some embodiments of the present apparatuses further comprise: a pH sensor coupled to the catheter; where the catheter is further configured to be coupled to a controller such that the controller can receive pH signals from the pH sensor. Some embodiments of the present apparatuses further comprise: a transverse ultrasonic transducer pair coupled to the catheter; where the catheter is configured to be coupled to a controller such that the controller can receive ultrasonic signals from the transverse ultrasonic transducer pair. Some embodiments of the present apparatuses further comprise: a controller configured to be coupled to the catheter such that the controller can receive signals from the longitudinal ultrasonic transducer pair, and from the transverse ultrasonic transducer pair, the controller further configured to determine from the ultrasonic signals an indication of esophageal volume, and an indication of reflux volume during a gastroesophageal reflux event of a patient.

In some embodiments of the present apparatuses, at least transducer of each transducer pair is configured to emit ultrasonic signals at a frequency at or above 1 MHz.

In some embodiments of the present apparatuses, the catheter is configured to be disposed within an esophagus of a patient such that the transducer is disposed at or a distance above the patient's lower esophageal sphincter (LES), and the controller is configured to determine a first radius of the esophagus based the ultrasonic signals received from the longitudinal transducer pair, and a second radius of the esophagus based on ultrasonic signals received from the transverse transducer pair. In some embodiments, the controller is configured to determine an indication of reflux volume during a GER event by modeling at least a portion of the esophagus (e.g., between the spaced longitudinal transducer pair) as revolved trapezoidal tank having the first radius and the second radius.

In some embodiments of the present apparatuses, the controller is configured to filter at least one of the signals received from the ultrasonic transducer pairs, and the indications of reflux volume determined, to remove events having a duration below a threshold duration. In some embodiments, the threshold duration is greater than 2 seconds. In some embodiments, the threshold duration is greater than 5 seconds.

In some embodiments of the present apparatuses, the controller is configured to rectify the signal received from the longitudinal ultrasonic transducer pair.

In some embodiments of the present apparatuses, the controller is configured to identify reflux events based on reductions in amplitude of the signal received from the longitudinal ultrasonic transducer pair.

Some embodiments of the present methods comprise: receiving ultrasonic signals from a spaced longitudinal ultrasonic transducer pair disposed within a patient's esophagus; and determining from the ultrasonic signals an indication of reflux volume during a gastroesophageal reflux event of the patient. In some embodiments, determining an indication of reflux volume includes modeling at least a portion of the esophagus as a cylindrical lumen having a radius determined from the ultrasonic signals received from the longitudinal ultrasonic transducer pair. Some embodiments further comprise: receiving ultrasonic signals from a transverse ultrasonic transducer pair disposed within a patient's esophagus; and determining from the ultrasonic signals an indication of esophageal volume.

Some embodiments of the present methods further comprise: disposing a catheter having a spaced longitudinal ultrasonic transducer pair in the esophagus of a patient such that at least one transducer of the longitudinal ultrasonic transducer pair is disposed a distance above the patient's lower esophageal sphincter (LES). In some embodiments, the catheter also has and a transverse ultrasonic transducer pair, and the catheter is disposed such that the transverse ultrasonic transducer pair is disposed a distance above the patient's LES.

In some embodiments of the present methods, determining an indication of reflux volume comprises: determining a first radius of the esophagus based on ultrasonic signals received from the longitudinal ultrasonic transducer pair; and determining a second radius of the esophagus based on ultrasonic signals received from the transverse ultrasonic transducer pair. In some embodiments, determining an indication of reflux volume further comprises: determining an indication of reflux volume during a GER event by modeling at least a portion of the esophagus as revolved trapezoidal tank having the first radius and the second radius.

Some embodiments of the present methods further comprise: filtering the signals received from the ultrasonic transducer pairs to remove events having a duration below a threshold duration. In some embodiments, the threshold duration is greater than 2 seconds. In some embodiments, the threshold duration is greater than 5 seconds.

Some embodiments of the present methods further comprise: rectifying the signals received from the ultrasonic transducer pairs.

Some embodiments of the present methods further comprise: identifying one or more reflux events based on one more reductions in amplitude of the signals received from the longitudinal ultrasonic transducer pair.

Any embodiment of any of the present devices and kits can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

DESCRIPTION OF ILLUSTRATIVE EMBODIMENTS

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a device or kit that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps. Further, a device, system, or structure that is configured in a certain way is configured in at least that way, but it can also be configured in other ways than those specifically described.

Figure 1:
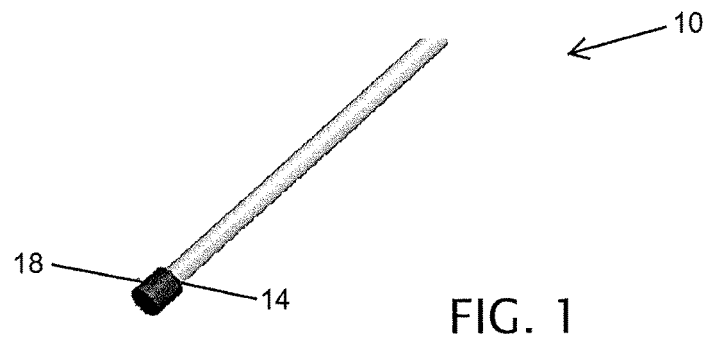
FIG. 1 depicts an embodiment of the present ultrasonic catheter (having a longitudinal ultrasonic transducer) that is suitable for some embodiments of the present methods.

Referring now to the drawings, and more particularly to FIG. 1, shown therein and designated by the reference numeral 10, is one of the present embodiments of ultrasonic catheters suitable for monitoring reflux volume during a gastroesophageal reflux event of a patient. In the embodiment shown, catheter 10 has a proximal end (not shown), a distal end 14, and a longitudinal ultrasonic transducer 18 coupled to distal end 14. The proximal end (not shown) of catheter 10 is configured to be coupled to a controller (e.g., a processor, computer, or other data acquisition and/or processing device), such as, for example, via a plug or other suitable connector. As used in this disclosure, a longitudinal ultrasonic transducer or transducer pair has a central axis that is substantially parallel to the longitudinal axis of the catheter when the catheter is straight. As used in this disclosure, a transverse ultrasonic transducer or transducer pair has a central axis that is substantially perpendicular to the longitudinal axis of the catheter when the catheter is straight.

Embodiments of the present methods use the ultrasonic transducer for echo ranging to monitor the media around it and the discontinuity or the interface along the propagation media. For instance, a pulsed ultrasonic wave transmitted through water towards an interface composed of water and soft tissue will be reflected and detected by the same transducer after a certain elapsed time. Accordingly, the distance between the transducer and the tissue can be inferred from Equation (1) (see also reference [9]):

$$D = V_S T_E \tag{1}$$

where D is the round trip distance, $V_S$ is the velocity of sound in water, and $T_E$ is the elapsed time.

Figure 2A:
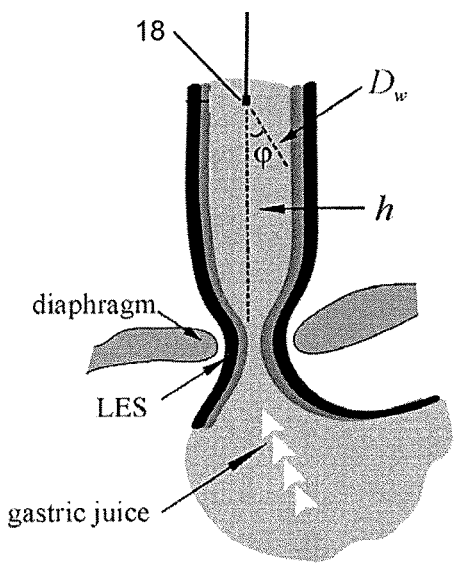
FIG. 2A depicts the position of the ultrasonic transducer for some embodiments of the present methods.
Figure 2B:
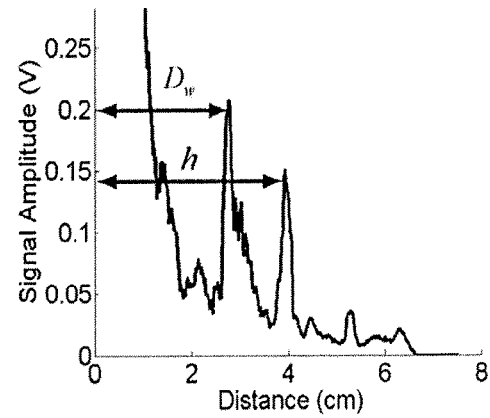
FIG. 2B depicts a chart of ultrasonic signal amplitude for the transducer in the position of FIG. 2A.

FIG. 2A depicts the position of transducer 18 within a patient's esophagus for some embodiments of the present methods, and FIG. 2B depicts a chart of ultrasonic signal amplitude for transducer 18 in the position of FIG. 2A. As illustrated, some embodiments of the present methods utilize longitudinal ultrasonic sensing to detecting distension of distal esophagus provoked by gastric content present in the esophageal lumen (e.g., during gastroesophageal reflux events). During the normal or resting state, the walls of the distal esophagus are collapsed and the lower esophageal sphincter (LES) is closed. In this state, ultrasonic waves sent by the transducer are reflected from the nearby esophageal wall. The presence of gastric content in the esophageal lumen prolongs the time for the ultrasonic waves to be reflected from the esophageal wall. These changes of the echoes can then be extracted from the ultrasonic system as an indicator of the presence of GER content.

If one or more diameters of the distal esophagus (esophageal lumen) during a GER event are measured dynamically, an estimation of the reflux volume can be obtained with some approximations and assumptions. The first important assumption is that the reflux volume from the tip of the catheter down to the LES is correlated with the total amount of reflux. The second assumption is to consider the distal esophagus shape to be symmetrical about one of its axes. The third one is that reflux dynamics can be modeled by a mathematic function.

A model of the esophageal lumen which has been frequently used in esophageal bolus transport simulation is a cylinder [22]. This cylindrical model could also be used for modeling reflux content dynamics when distal esophageal lumen is distended during reflux episodes. The volume of this model V can be calculated according to Equation (2):

$$V = \frac{1}{4} \times D^2 \times h \times \pi \tag{2}$$

where D is the transverse distal esophageal diameter and h is the length between transducer and the LES. As illustrated in FIG. 2A, the measurement of D can be obtained by with a longitudinal ultrasonic sensor with an angle of divergence φ:

$$D = D_w \times \sin\phi \times 2 \quad (3)$$

where $D_w$ is the distance between the transducer and the esophageal wall along a line at the angle of divergence of the transducer.

Figure 3:
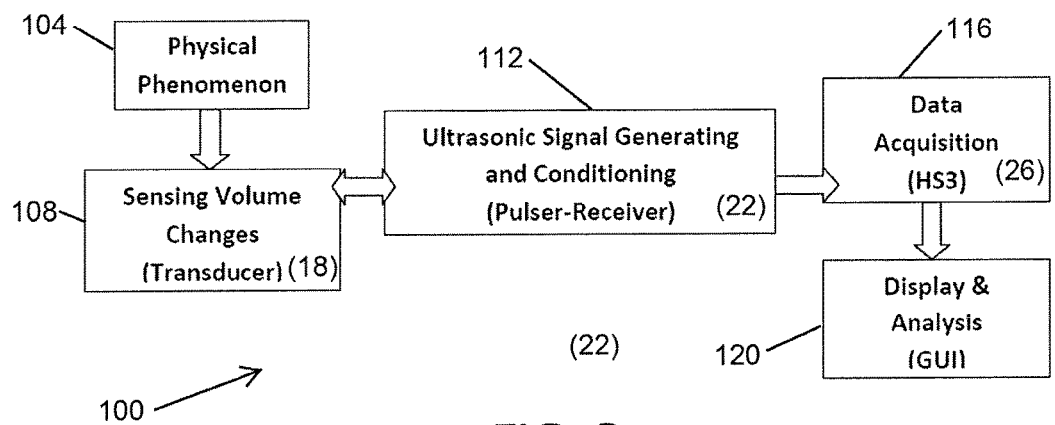
FIG. 3 depicts a conceptual block diagram and flowchart for one embodiment of the present systems.

FIG. 3 depicts a conceptual block diagram and flow chart of the ultrasonic system 100 and certain of the present methods. At a step 104, a physical phenomena (e.g., a gastroesophageal reflux event occurs). At a step 108, the phenomena (or resulting characteristics or changes) are measured (e.g., with transducer 18). In the embodiment shown and used for certain of the tests described in this disclosure, catheter 10 had a diameter of 1.4 millimeters (mm), and transducer 18 had a diameter of 2.54 mm and a height of 2.54 mm. In the embodiment tested, the central frequency of the ultrasonic transducer was 2 MHz, and had a resulting resolution of 0.38 mm, which proved to be precise enough for sensing volume changes in the distal esophagus.

Ultrasonic catheter 18 was manufactured by Valpey Fisher Corporation (Hopkinton, Mass., USA), and was coupled to a CompactPulser ultrasonic signal conditioner 22 (US Ultratek Inc, Concord, Calif., USA). In other embodiments, any suitable ultrasonic condition can be used. The catheter cable connecting the transducer to the signal conditioner had a diameter of 1.4 mm. At step 112, signal conditioner 22 drives transducer 18 to transmit ultrasonic energy (waves or signals, e.g., by exciting the transducer) and receive ultrasonic signals indicative of the reflected energy (e.g., echo signals that originate from the transducer and are reflected back to the transducer). Ultrasonic signal conditioner 22 was configured to excite transducer 18 with a low-power electrical pulse of 200 Volts and duration of 200 nanoseconds (ns), such that the crystal in the transducer resonated at 1 MHz and acted as both transmitter and receiver. The echo signals were amplified 78 dB.

In the embodiment tested, conditioner 22 was coupled to an HS3 USB oscilloscope 26 (Tiepie Engineering, WL SNEEK, The Netherlands). In other embodiments, any suitable oscilloscope or circuitry with similar function may be used. For the tests described in this disclosure, a sampling rate of 5 MS/s was used. In other embodiments, any suitable sampling rate can be used, such as, for example, a sampling rate equal to, greater than, less than, or between, any of: 1, 2, 3, 4, 6, 7, 8, 9, 10, or more MS/s. At step 116, oscilloscope 26 received the acquired data from conditioner 22 and transferred the acquired data to a computer (PC) 30 through a USB port.

At step 120, computer 30 received, processed, and displayed results determined from, the data from oscilloscope 26. In the embodiment tested, computer 30 comprised a PC running Matlab (MathWorks Inc, Natick, Mass.) which had been configured to provide a graphical user interface (GUI) for device control, data acquisition, signal processing, and monitoring of results from transducer 18, as described in more detail below. In other embodiments, any suitable controller can be used for signal acquisition, conditioning, and/or processing. For example, a controller or control system can include a processor, a CPU, a signal conditioner, an oscilloscope or other data acquisition device, and/or instructions for determining an indication of reflux volume from received signals (e.g., in a self-contained unit that may include a user display such as a screen, or that may be coupled to a monitor, television, or other display device).

The signal processing algorithm for the tested embodiment included a reflux detection stage and reflux volume estimation stage. For reflux detection, the mean value of the echo amplitudes received from the nearby interfaces was determined. This mean value generally decreases as the reflux develops and can be calculated according to Equation (4):

$$x(n) = \frac{1}{R}\int_0^R A_n(m)dm \quad (4)$$
$$n = 0, 1, \ldots, N-1$$

where x(n) is the output sequence extracted from multiple ultrasonic waveform frames; $A_n(m)$ is the amplitude of the echo from a certain distance m in the current sampling waveform; and R determines the distance range of the nearby interfaces for calculating the mean amplitude. As described in more detail below, R was determined by placing ultrasonic catheter 10 into a gastroesophageal model (200 in FIG. 5) during simulated reflux events and comparing the corresponding waveforms with the waveforms acquired during non-reflux state. By repeating this procedure 10 times, an optimal value of the distance was found equal to 2 cm.

Figure 4:
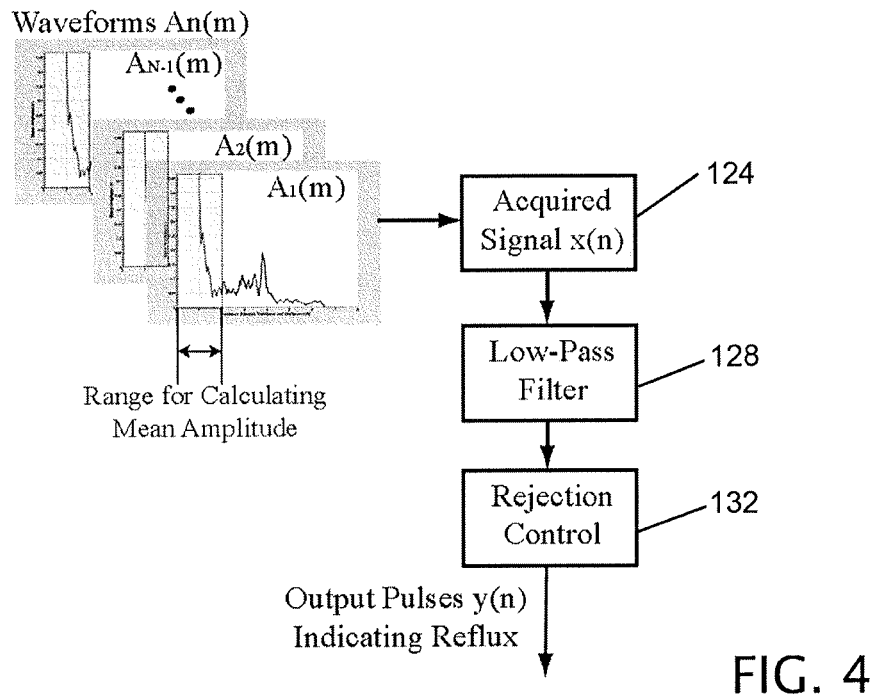
FIG. 4 depicts a flowchart of one of the present filtering algorithms that is suitable for some embodiments of the present methods and systems.

FIG. 4 depicts a flowchart of the signal processing steps for some embodiments of the presents methods and systems. In step 124, the mean value of the echo amplitudes is determined, as described above and indicated by Equation (4). When the catheter is intubated into the esophagus of a patient, the ultrasonic transducer may respond not only to reflux events, but to other events (e.g., coughing, belching and respiration) as well. To minimize the effects of such other events, at step 128, the acquired signal x(n) was initially subjected to a filtering stage which focused on amplifying the response characteristic of the reflux events. The embodiment tested utilized a 10th-order Butterworth low-pass filter with a passband frequency of 0.2 Hz, which was selected to reflect the assumption that the duration of one reflux episode in a patient is generally longer than 2.5 seconds. Next, step 132 includes a rejection control function to identify and/or extract time points at which the echo signals are smaller than a threshold value (e.g., threshold echo value prior to the beginning of a reflux event, such as when the esophagus is in a normal or relaxed state and the LES is closed), which indicates the presence of reflux.

Once reflux events are identified, the reflux volume estimation stage determines an indication (e.g., calculates an approximation) of reflux volume. For example, in the embodiment tested, the volume estimation algorithm comprises peak-detection algorithm, which performs the estimation of the diameter and the height of the reflux model, as described above with reference to Equations (1)-(3) and FIGS. 2A and 2B. More particularly, the peak-algorithm identifies the signal amplitude peaks that correspond to $D_w$ and h. $D_w$ can be correlated to the esophagus diameter, D; and h, in turn, can be correlated to the distance between the ultrasonic transducers and the patient's LES. The approximate volume of the relevant portion of the esophagus (and thus, the reflux volume) can then be determined using the cylindrical model. When refluxate extends above the transducer, the amount of reflux volume can be estimated utilizing the already estimated reflux volume below the transducer and the proximal extent of reflux registered by simultaneous multichannel impedance recording, with the assumption that the radial diameter of the esophageal tube above the transducer remains approximately the same. For example, the known distance between or vertical positions of the impedance sensors can be used to approximate the height of the cylinder model and thereby determine an indication of refluxate volume in the esophagus.

1. In Vitro Testing

Figure 5:
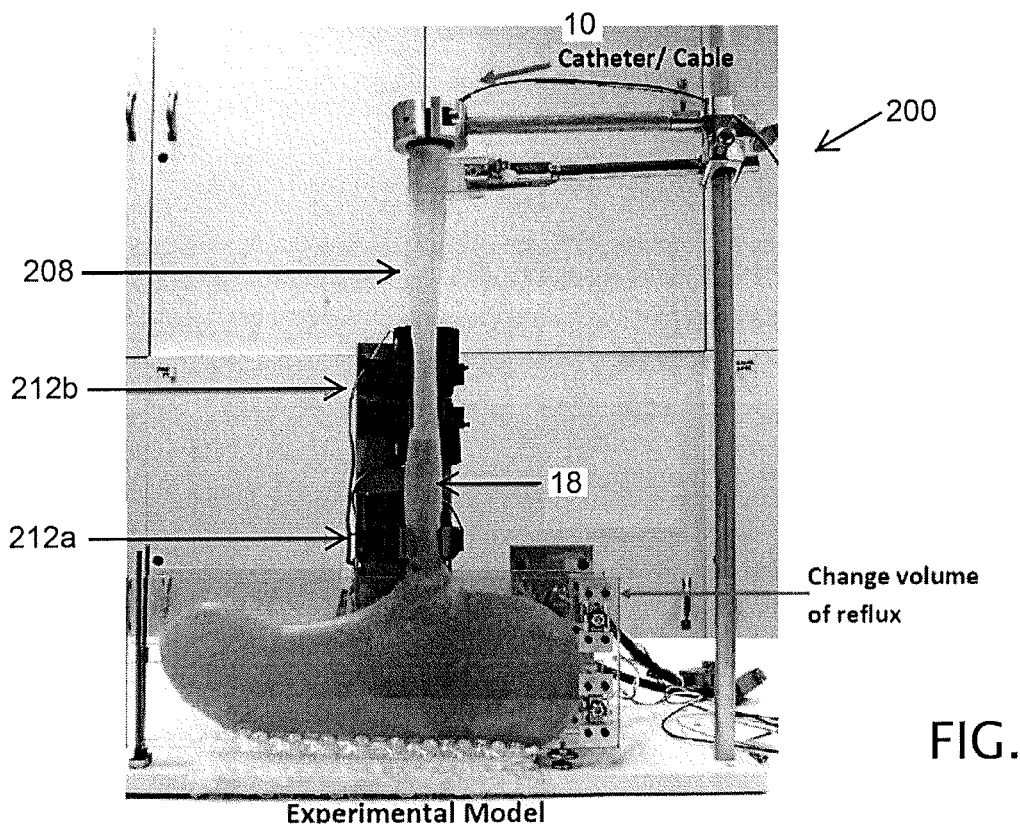
FIG. 5 depicts a test apparatus used to test some embodiments of the present methods and systems.

Referring now to FIG. 5, to quantify the performance of the ultrasonic catheter and to determine its suitability for in vivo testing in the esophagus, a series of in vitro tests were performed. To test the response of the ultrasonic system to reflux volume, an experimental model 200 was built to simulate the motility of the distal esophagus as well as the dynamics of gastroesophageal reflux. Model 200 included a silicone stomach model 204 (Simulab Corporation, Seattle, Wash., USA) having a model esophagus 208. Two automatically controlled clamps 212a, 212b were used to produce controllable pressure to simulate gastroesophageal reflux with repeatable strengths and duration. To improve observation, clamps 212a and 212b were transparent and comprised synthetic glass. Stomach model 204 was filled with acidic solution with added blue food coloring to distinguish the reflux material. For testing, ultrasonic catheter 10 (transducer 18) was positioned a distance of about 5 centimeters (cm) above lower gripper 212a to monitor the shape changes of the experimental model. Using model 200, measurements from the ultrasonic system were correlated to the shape of the distal portion of esophagus 208 and reflux volume. Although the material of the experimental model was different from esophageal lining, the movement of reflux material was effectively simulated.

Reflux episodes were simulated to test the sensitivity of the ultrasonic system. More particularly, external forces were applied to model esophagus 208 with lower gripper 212a to change the shape of (constrict) esophagus 208. Transducer 18 of ultrasonic catheter 10 was placed 5 cm above lower gripper 212a to simulate the position of transducer 18 at about 5 cm above a patient's LES. In other embodiments, transducer 18 can be positioned at any suitable distance above a patient's LES (e.g., equal to, less than, or between, any of: 1, 2, 3, 4, 6, 7, 8, 9, 10, or more centimeters above the LES). Simulation of gastroesophageal reflux was performed using experimental model 200. Controlled by clamps 212a, 212b, the distal portion of model esophagus 208 was first empty and collapsed around ultrasonic transducer 18 for three (3) seconds. Then, the simulated reflux material flowed into the esophageal model and the transducer was submerged for 5 seconds. After that, the material flowed into the stomach section of the model to simulate the end of the reflux event. These changes simulated LES relaxation and gastroesophageal reflux.

These initial tests verified that simulated reflux episodes could be effectively detected by the ultrasonic catheter system. Once reflux events were identified via the known position of transducer 18 relative to (e.g., 5 cm above, as tested) the LES (lower gripper 212a), the volume of the distal esophagus can be estimated between the position of the sensor and the LES based on the echo peaks (example charted in FIG. 2B). As such, the ultrasonic catheter system can be used to monitor the dynamics of the reflux volume in the esophagus.

Different volumes of reflux were then simulated in model 200 to test the present ultrasonic catheter system and methods. The transducer was positioned about 5 cm above the lower gripper 212a (LES), which was left partially open. The diameter of model esophagus 208 between the transducer and lower gripper 212a (LES) was set to 2 cm for a first experimental trial, and was set to 1 cm for a second experimental trials. In each simulated reflux event, the simulated refluxate was introduced into the model esophagus 208 until the simulated refluxate submerged or covered the ultrasonic transducer (18). The volume of the simulated refluxate was then measured by a measuring cup. The ultrasonic system showed good repeatability and accuracy in detecting the simulated reflux events, and in estimating the reflux volume from the transducer down to lower gripper 212a (LES), as shown in Table 1.

TABLE 1

Summary of Laboratory Bench Results

| | Trial 1 | Trial 2 |
|---|---|---|
| Trial length (minutes) | 5 | 5 |
| Total simulated reflux events | 30 | 30 |
| Reflux events detected correctly | 30 | 30 |
| Reflux volume (ml) (Using a measuring cup) | 12 | 5 |
| Measured diameter (cm) | 1.80 ± 0.24 | 1.22 ± 0.14 |
| Measured height (cm) | 3.99 ± 0.46 | 3.61 ± 0.31 |
| Measured volume (ml) | 10.62 ± 2.62 | 4.24 ± 1.12 |

2. In Vivo Human Testing

In vivo human testing was performed over a one-hour period on a volunteer subject to obtain initial results of the system response to actual reflux dynamics. A high resolution esophageal manometry probe was intubated through the subject's left nostril to locate the position of the subject's LES. The manometry probe was then removed and an MII-pH impedance probe (ZAN-BS-01ComforTec Z/pH catheter (Sandhill Scientific Inc, Highlands Ranch, Colo.) was inserted through the subject's left nostril. The tested embodiment of ultrasonic catheter 10 was then inserted through the subject's right nostril. According to manometrically determined position of the LES, the tip of catheter 10 (i.e., distal end of transducer 18) was positioned at a distance of approximately 5 cm above the subject's LES. The two probes were then secured to the subject at the point of entry. During the tests, both liquid and gas reflux were indicated from the MII-pH system, which was used to calibrate the ultrasonic system and evaluate its responses to the MII-pH registered reflux events. Sensor responses were monitored as the subject experienced a number of events that included: heartburn, belching and swallowing. The events occurred in random order, and were registered on both the ultrasonic system and the MII-pH system recordings.

Figure 6:
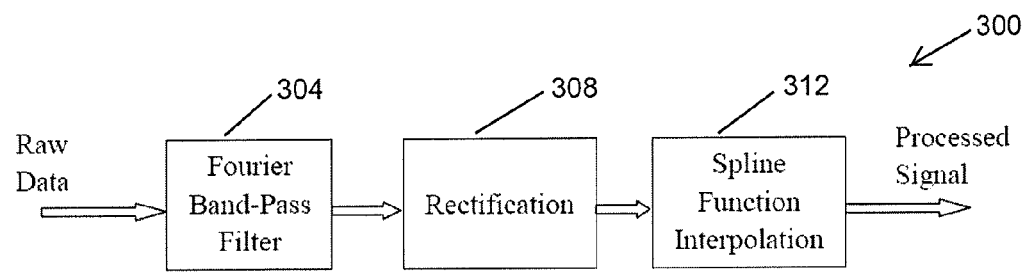
FIG. 6 depicts a flowchart of another one of the present filtering algorithms that is suitable for some embodiments of the present methods and systems.

During the in-vivo study, the subject experienced a series of events (i.e. cough, swallowing, heartburn and belching) in a random order while the response of the ultrasonic transducer was monitored and recorded. The raw data acquired by the ultrasonic catheter was subjected to a filtering process 300 that differed in some respects to the filtering process described above with reference to FIG. 4. As depicted in the flowchart of FIG. 6, filtering process 300 included several filtering stages were configured to amplify the response characteristic of reflux events, and to reduce the response resulting from respiration and heartbeat. At step 304, the acquired echo measurement was first subjected to a Fourier band-pass filter having a lower cut-off frequency of 0.016 Hz and a higher cut-off frequency of 0.2 Hz, which was based on the assumption that the duration of one reflux episode in the subject lasted about 5-60 seconds. This band-pass filter attenuates baseline drift and signal variations which are not related to reflux events, such as those resulting from respiration and heartbeat. At step 308, the signal was next rectified to convert negative portions of the signal to zero. Finally, at step 312, the signal is smoothed with an interpolating spline function or the like. In the tested embodiment, the peaks of the signal were enveloped using the standard interpolating spline function of Matlab), resulting in a signal that is more easily understood visually, and is therefore better suited for display.

Figure 9:
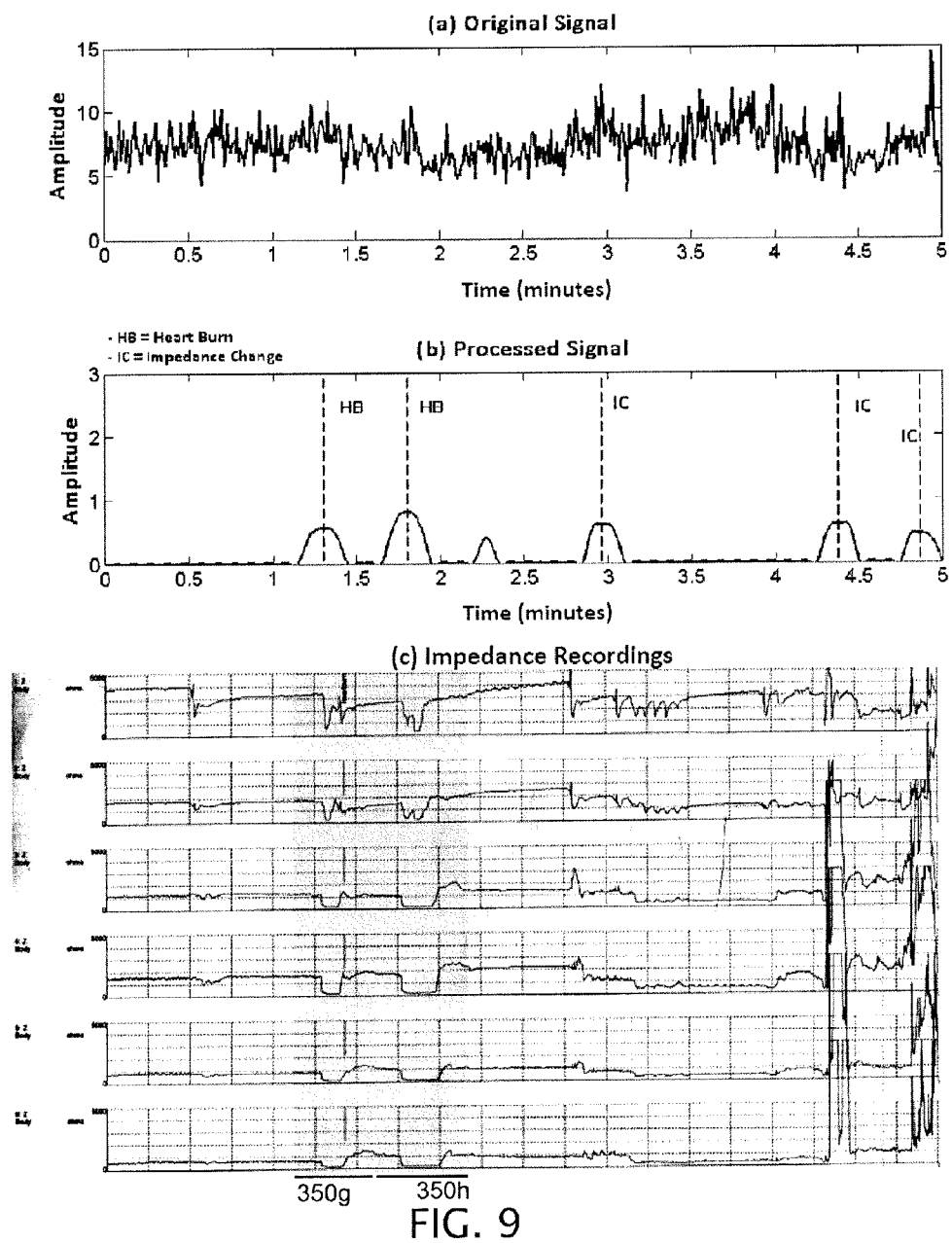

The MII-pH impedance catheter was coupled to Bio-view Analysis software (Sandhill Scientific Inc, Highlands Ranch, Colo., USA). Both liquid and gas reflux episodes were identified from the physiological recordings obtained with the impedance catheter. Confirmation of reflux episodes was also performed manually. The results from the MII-pH and manual event recorder were synchronized and compared with the results from the ultrasonic system. Samples of the study are shown in FIGS. 6-9. FIG. 9 was recorded while the subject was sitting, while the other three figures were recorded while the subject was in supine position. In each figure, (a) shows the raw data from the ultrasonic catheter output, (b) shows the processed data obtained by filtering the raw data with filtering process 300, and (c) shows the simultaneous recordings of the MII-pH impedance system at each of five difference electrodes along the length of the impedance catheter. In these samples, it can be observed that both liquid/gas reflux and most of the impedance changes were consistently identifiable from the processed ultrasonic data. The variation of the ultrasonic system output indicated that the propagation media of the ultrasound was changing in the distal esophagus, which was also detected by the impedance system at the same time. Additionally, the amplitude of the ultrasonic data provided information about the reflux volume.

As noted above, FIG. 7(a) charts the raw ultrasonic signal, FIG. 7(b) charts the processed ultrasonic signal, and FIG. 7(c) charts impedance recordings for a first sample time period. The shadowed regions 350a-350d in FIG. 7(c) indicate the reflux events distinguished by the Bio-view Analysis software. The notation HB indicates heartburn events detected by the MII-pH impedance probe and confirmed by the manual record. The impedance dynamics and reflux volume in the distal esophagus are illustrated by the ultrasonic signal. FIG. 8(a) charts the raw ultrasonic signal, FIG. 8(b) charts the processed ultrasonic signal, and FIG. 8(c) charts impedance recordings for a second sample time period. The dynamics of ultrasonic data within the first two (2) minutes show that the amplitude of the signal changed from high to low, which indicated a reflux-volume change from a relatively small volume to a relatively large volume. Additionally, the heartburn event was indicated by the ultrasonic data when reflux volume reached its maximum. The shadowed regions 350e-350f in FIG. 8(c) indicate the reflux events identified by the Bio-view software. FIG. 9(a) charts the raw ultrasonic signal, FIG. 9(b) charts the processed ultrasonic signal, and FIG. 9(c) charts impedance recordings for a third sample time period. As indicated by the impedance readings, two gas reflux events happened within the last minute. Although these changes were also detected by the ultrasonic system, the difference between liquid- and gas-induced impedance changes are difficult to distinguish. The shadowed regions 350g-350h in FIG. 9(c) indicate reflux events identified by the Bio-view software.

Figure 10:
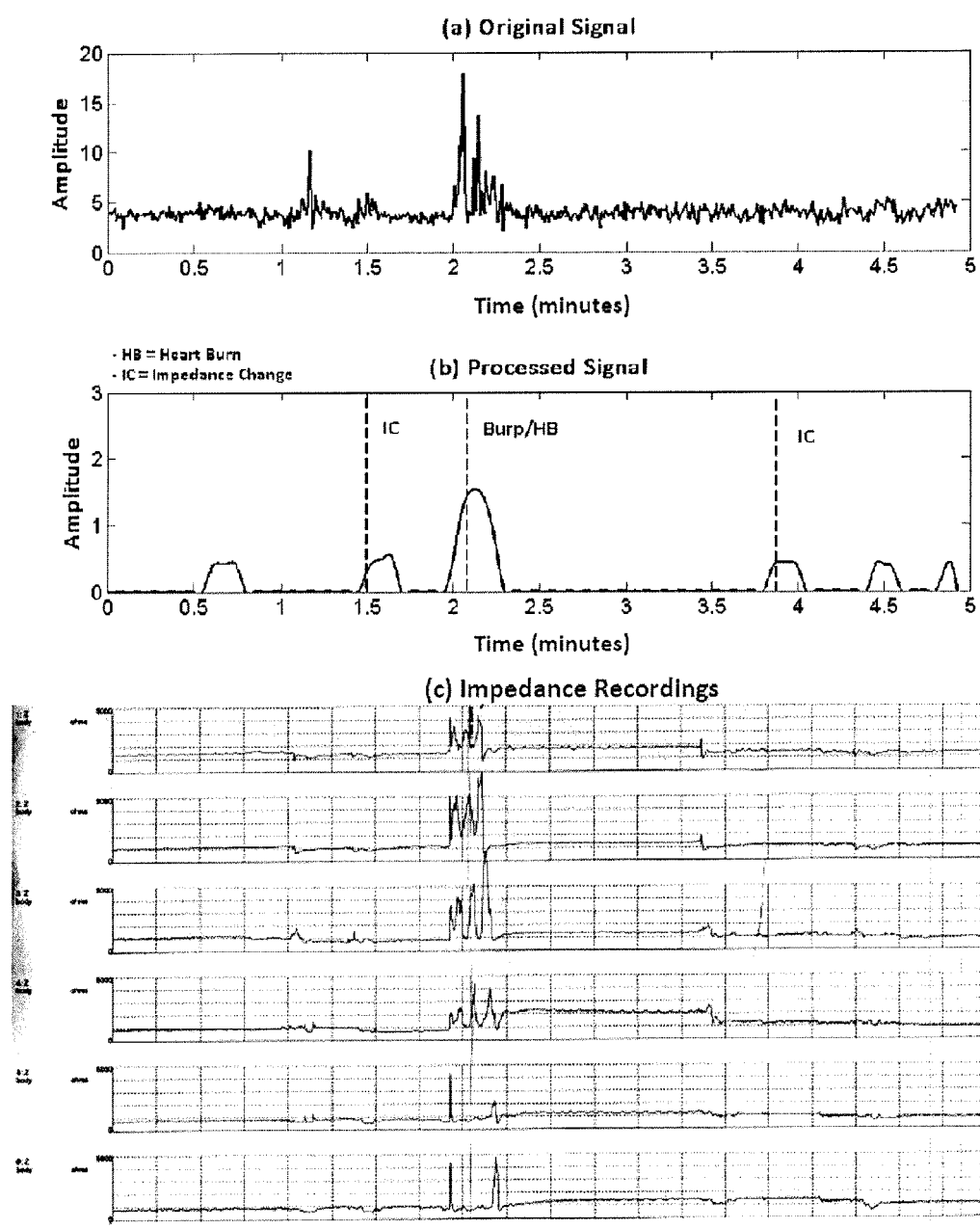

As noted above, FIG. 10(a) charts the raw ultrasonic signal, FIG. 10(b) charts the processed ultrasonic signal, and FIG. 10(c) charts impedance recordings for a fourth sample time period. One heartburn with a belching episode happened, and the impedance output changed accordingly. This dynamics was also observed using the ultrasonic system. However, there were some amplitude changes in the ultrasonic signal that could not be related to obvious impedance variations. It is believed that this changes were due to the influence from the MII-pH impedance catheter, because the ultrasonic probe and impedance catheter were could not be kept in entirely fixed relation to one another during the tests.

Figure 11:
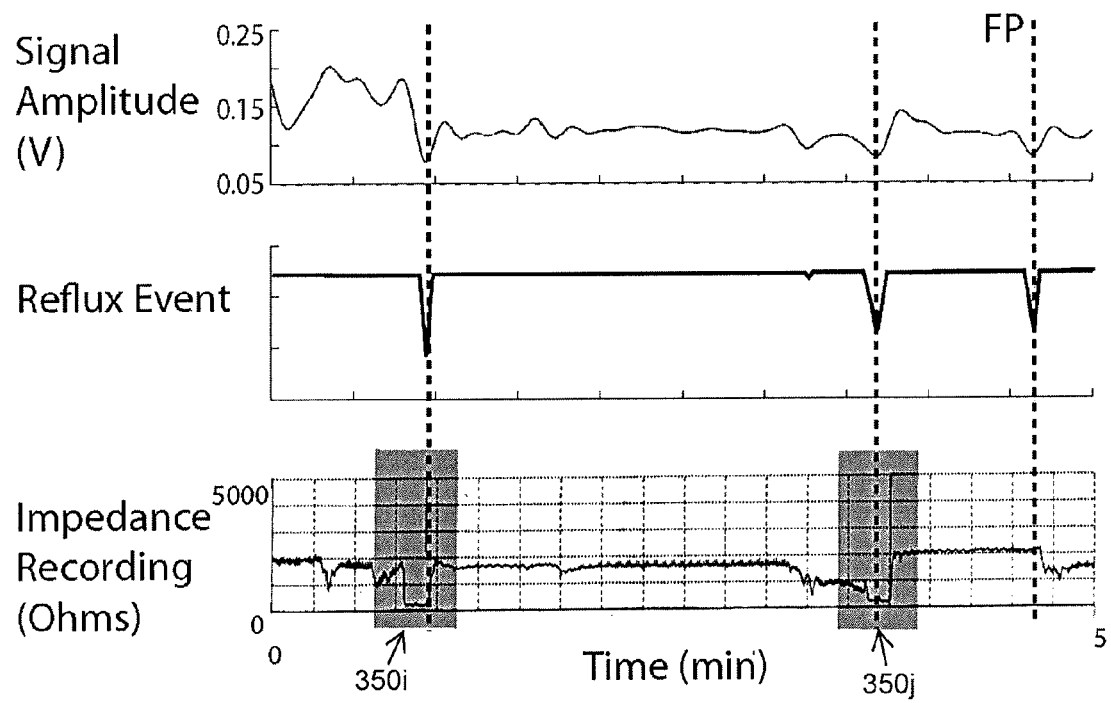
FIGS. 7-11 chart data gathered through tests of embodiments of the present methods and systems.
Figure 7:
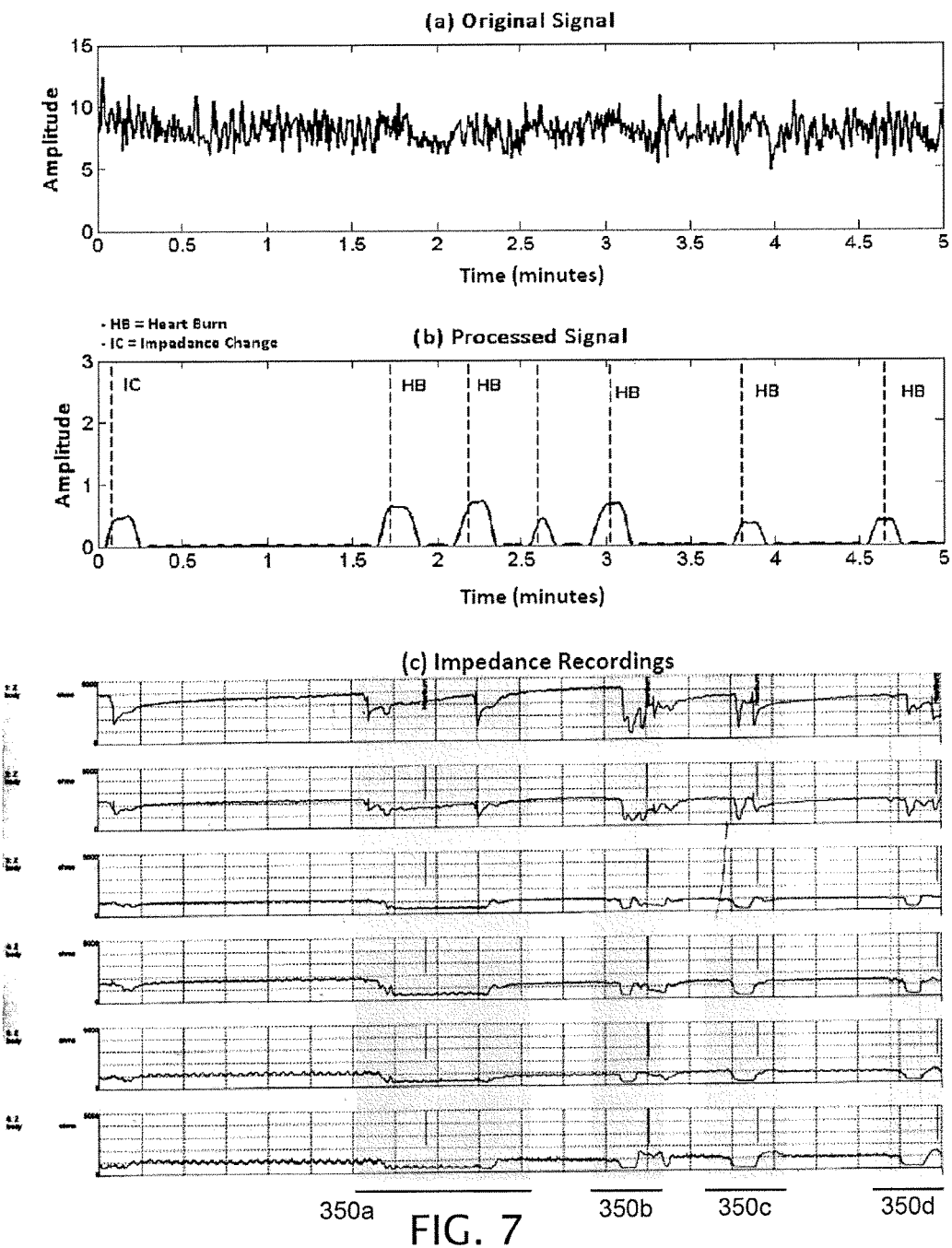
Figure 8:
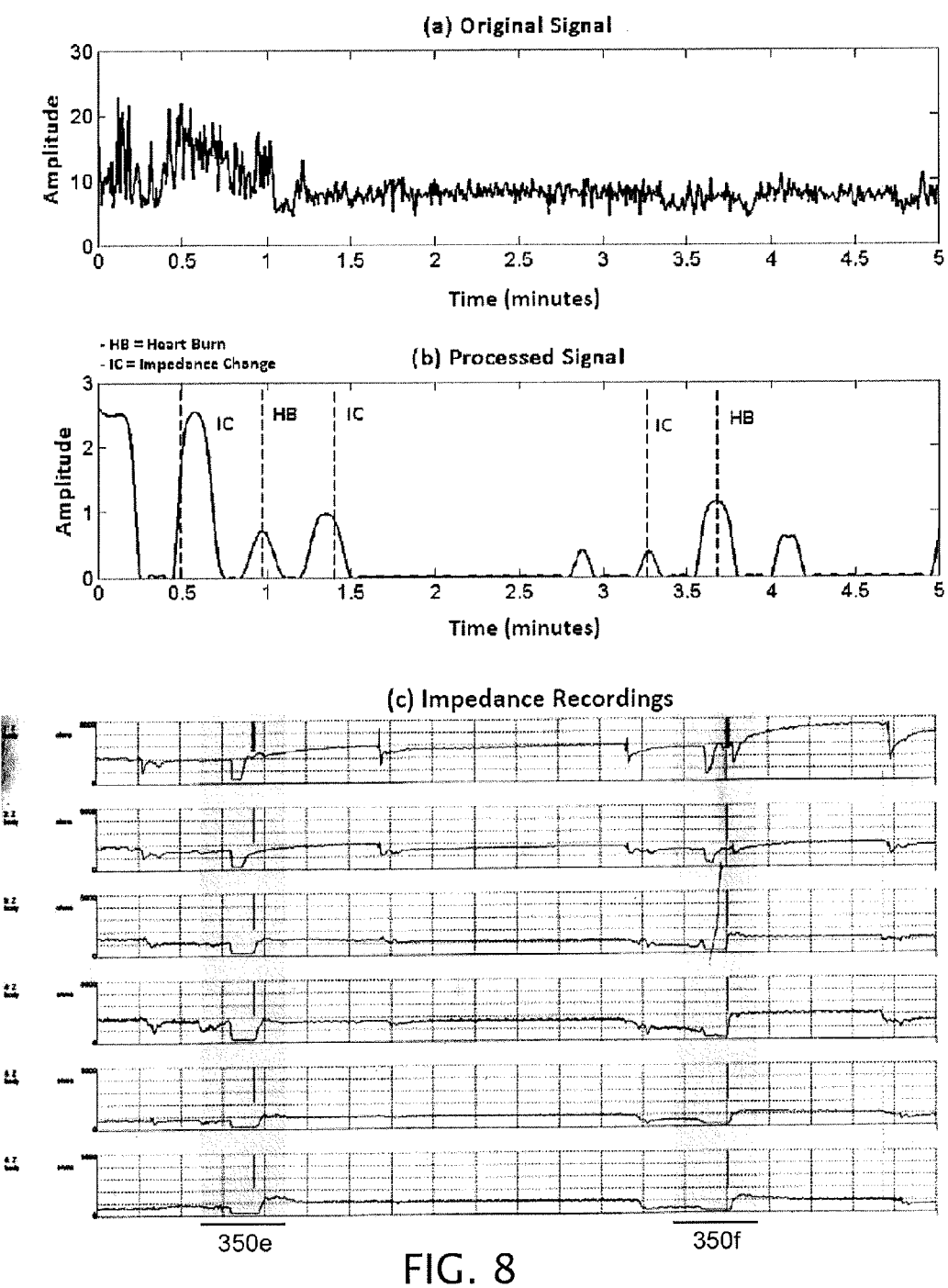

During the test, reflux events were successfully identified by the ultrasonic system compared to the impedance recording, as shown in Table 2. Additionally, and as shown in FIG. 11, dynamic ultrasonic changes associated with reflux presence were observed. As listed in Table 2, eight of ten spontaneous reflux events were identified correctly, as verified by the MII impedance system. However, six false positives were detected by the ultrasonic system out of an overall sixteen (16) impedance-changing events. There were two false negatives, likely due to relative movement between the ultrasonic catheter and the MII-pH catheter. Reflux volume from the transducer down to the LES during the testing calculated by the ultrasonic method was 4.12±0.82 ml.

TABLE 2

| Summary of In vivo Human Testing Results | |
|---|---|
| Total impedance changes | 16 |
| Total reflux events (MII) | 10 |
| Reflux events detected correctly | 8 |
| Reflux event false negative | 2 |
| Reflux event false positive | 6 |

The tests demonstrate that the present ultrasonic catheter methods and systems are sensitive to random liquid volume changes, and indicate good repeatability. During the tests, the computer-based signal acquisition system was also able to process the ultrasonic signal and display the data in substantially real-time. The in vivo results further show good sensitivity to the dynamics of the distal esophagus and reflux volumes. In fact, respiration and heartbeat may also contribute to the output of the ultrasonic system, but these can be reduced by various embodiments of the signal processing (filtering) methods described above. In the experiments, the GER events were identified by decreases in ultrasonic signal amplitude, which normally appeared when the ultrasonic transducer contacted the refluxate. Reflux volume estimation results compared very well with the results measured by independent objective techniques during in vitro testing. However, for optimal measurement of esophageal diameter, the longitudinal transducer should be positioned at the cross-sectional center of the esophagus, and movement of the transducer may adversely affect the measurement. As such, some embodiments of the present ultrasonic catheters comprise a longitudinal ultrasonic transducer with a large angle of divergence (e.g., equal to, greater than, or between, any of: 45, 50, 55, 60, 65, 70, 75, 80, 85, or more degrees); and/or are configured to obtain the average of the elapsed periods of two echo peaks that may be detected if the transducer is not perfectly centered in the esophagus, and determine the diameter based on this average.

Most of the time, the processed data from the ultrasonic catheter was sufficient to distinguish reflux-induced esophageal distension and estimate corresponding variations in the reflux volume. Exceptions may be attributed to the random movements of the impedance probe relative to the ultrasonic catheter. Since the two catheters were separately inserted into the subject from different nostrils, the relative position of the two probes could not be monitored and controlled.

Thus, sound propagation could be affected when the ultrasound was randomly directed toward the impedance probe. It is anticipated that encapsulation techniques can be utilized to combine the two catheters into a single compact case. By doing this, the two probes could be introduced through one nostril using one catheter and the artifacts could be reduced. One embodiment 400 of the present integrated catheters is shown in FIG. 12.

Figure 12:
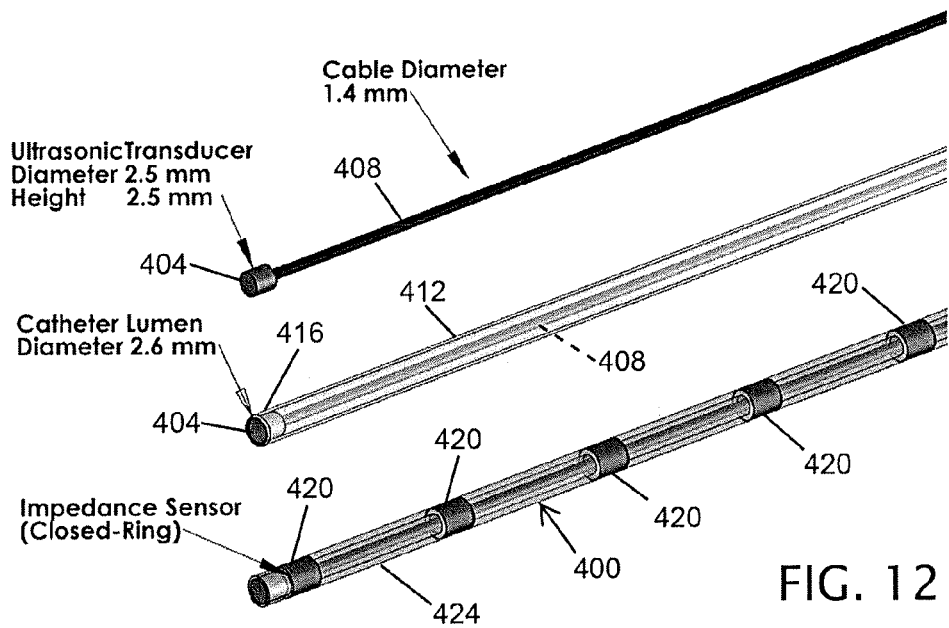
FIG. 12 depicts a perspective view of an embodiment of the present catheters.

FIG. 12 also illustrates a method for constructing catheter 400. In particular, an ultrasonic transducer 404 with cable 408 can be inserted into a catheter body 412 having an inner diameter that is substantially equal to the outer diameter of transducer 404. Ultrasonic transducer 404 can then be affixed to distal end 416 of catheter body 412 (e.g., with silicon or other adhesive. Conductive (e.g., comprising metal such as stainless steel) rings 420 having an inner diameter equal to the outer diameter of catheter body 412 can be used as impedance electrodes. Holes can be punched at desired locations for rings 420, and wires (not shown) comprising Copper or other suitably conductive material can be threaded through catheter body 412 and their respective holes. The wires can then be soldered (e.g., silver-soldered) or otherwise coupled to rings 420 (e.g., the interior faces of rings 420), and rings 420 can be coupled to catheter body 412 (e.g., to peripheral surface 424 of catheter body 412), such that rings 420 can serve as impedance electrodes. As shown, the integrated impedance/longitudinal ultrasonic catheter 400 has an ultrasonic transducer 404 coupled to distal end 416 of the catheter; and a plurality of electrodes 420 coupled in spaced relation along a length of peripheral surface 424 of the catheter (e.g., of catheter body 412). Additionally, in the embodiment shown, the proximal end (not shown) of catheter 400 is configured to be coupled to a controller (e.g., a controller configured to perform the signal processing and evaluation processes described above) such that the controller can receive impedance signals from electrodes 420 and ultrasonic signals from ultrasonic transducer 404. This integrated catheter 400 eliminated the possibility of a separate impedance catheter interfering with ultrasonic signals, and is configured to be intubated through a single nostril to reduce patient discomfort and simplify positioning of the catheter. The dimensions shown in FIG. 12 are examples of dimensions that are suitable for some embodiments of the present catheters, but are not limiting. For example, in other embodiments, any of the dimensions indicated in FIG. 12 (or elsewhere in this disclosure) may be increased or decreased by any of 10, 20, 30, 40, 50, 60, 70, 80, 90, or more percent.

3. Multichannel and Single Channel Ultrasonic Catheters

Figures 13A, 13B, 13C:
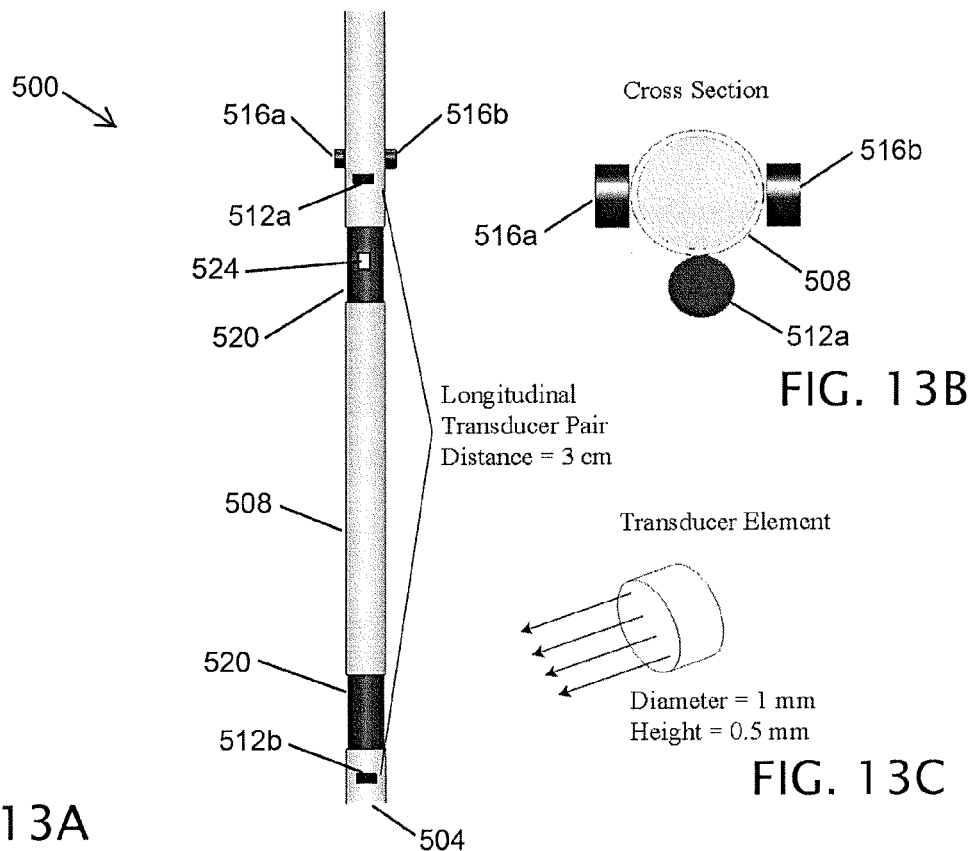
FIGS. 13A-13C depict various view of one embodiment of the present multi-channel ultrasonic catheters.

Referring now to FIGS. 13A-13C, another embodiment 500 is shown of the present ultrasonic catheters. In the embodiment shown, catheter 500 includes a proximal end (not shown), a distal end 504, and a peripheral surface 508. Rather than a single longitudinal ultrasonic transducer, catheter 500 includes a spaced (e.g., longitudinally spaced along a length of catheter 500) longitudinal ultrasonic transducer pair 512a, 512b coupled to peripheral surface 508 of catheter 500; and a transverse ultrasonic transducer pair 516a, 516b coupled to the peripheral surface 508 of catheter 500. In the embodiment shown, transverse ultrasonic transducer pair 516a, 516b are disposed at substantially the same longitudinal point along the length of catheter 500 (e.g., at substantially the same distance from distal end 504). In the embodiment shown, the proximal end of catheter 500 is configured to be coupled to a controller such that the controller can receive ultrasonic signals from longitudinal ultrasonic transducer pair 512a, 512b and from transverse ultrasonic transducer pair 516a, 516b. In the embodiment shown, catheter 500 further comprises a plurality of electrodes 520 coupled in spaced relation (spaced apart from each other) along a length of peripheral surface 508 of catheter 500; and proximal end (not shown) of the catheter is configured to be coupled to a controller such that the controller can receive impedance signals from the plurality of electrodes. In the embodiment shown, catheter 500 further comprises a pH sensor 524 coupled to catheter 500 (e.g., to peripheral surface 508); and proximal end (not shown) of the catheter is further configured to be coupled to a controller such that the controller can receive pH signals from pH sensor 524.

Catheter 500 can be described as a multichannel ultrasonic catheter, and may overcome some potential shortcomings of the single-channel ultrasonic catheter embodiments described above. In the embodiment shown, catheter 500 includes two ultrasonic transducer pairs. In a prototyped embodiment, LMT-510 ultrasonic pairs (Matec Instrument Companies. Northborough, Mass.) were used to fabricate the ultrasonic catheter. Each pair is configured to estimate one parameter of the cylindrical model, though may also contribute to estimating other parameters of the cylindrical model. Compared to the single-element catheter embodiments, the multichannel configuration of catheter 500 reduces the potential for false positives. Further, in the embodiment shown, catheter 500 integrates impedance electrodes (and thereby eliminates interference from a separate MII-pH impedance catheter). In the prototyped embodiment, medical grade heat-curing silicone adhesive MED1-4013 (NuSil Silicone Technologies, Carpinteria, Calif., USA) was used to attach the transducer pairs to a ZAN-BS-01 MII-pH impedance catheter (Sandhill Scientific, Highland, Colo., USA). The ultrasonic transducers were measured with a digital calliper to have diameters between 0.95 mm and 1.05 mm, and heights or thicknesses of about 0.5 mm.

This catheter consists of a transverse channel (transverse pair 516a, 516b) and a longitudinal channel (longitudinal pair 512a, 512b) for detecting GER episodes and measuring GER volume. In the prototyped embodiment, transverse transducers 516a, 516b were located 0.5 cm above pH sensor 524 on the MII-pH catheter and attached to opposite sides of the catheter using medical silicone. With this placement, catheter 500 can be intubated into the patient with the transverse channel (transverse pair 516a, 516b) at about 5.5 cm above the LES. For the longitudinal channel, upper transducer 512a is positioned 0.3 cm above pH sensor 524 and lower transducer 512b is positioned about 3 cm below upper transducer 512a. In other embodiments, lower and upper longitudinal transducers can be positioned at any suitable separation, such as, for example, equal to, greater than, or between, any of: 1, 1.2, 1.4; 1.6, 1.8, 2, 2.2, 2.4, 2.6, 2.8, 3.0, 3.2, 3.4, 3.6, 3.8, 4, 4.2. 4.4, 4.6, 4.8, 5, or more centimeters.

Figure 14:
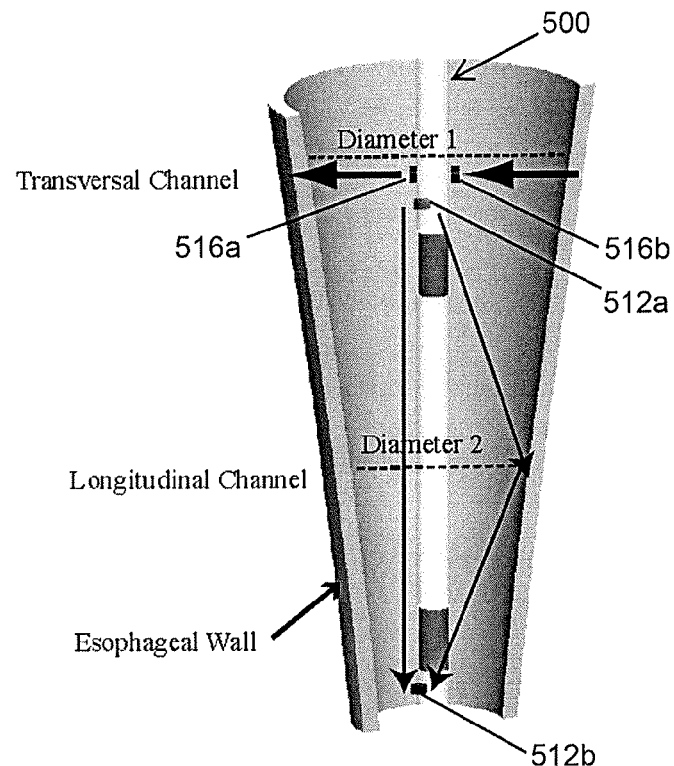
FIG. 14 depicts a perspective view of the catheter of FIG. 13A within a partially cutaway esophageal lumen.

In the prototyped embodiment, both of the longitudinal and transverse channels were configured for through-transmission mode ultrasound. In this mode, a first transmitter (e.g., upper longitudinal transducer 512a) sends ultrasonic waves, and a separate receiver (e.g., lower longitudinal transducer 512b) detects the amount of ultrasonic waves that reach its location after traveling through the medium surrounding the catheter (e.g., air, gas, refluxate, etc.). As with single-element detection, the through-transmission configuration is sensitive to the variation of the medium between the two transducers. Because the attenuation of the ultrasonic beam in human tissue or air is much larger than the attenuation in water or liquid material [9], it is possible to identify the occurrence of GER by monitoring the amount of ultrasound received from the transducer. Additionally, the echo signal received by the longitudinal channel can be used to dynamically determine the diameter of the esophageal lumen between the longitudinal sensors, and the diameter of the esophageal lumen at the transverse sensor pair, and thereby determine an indication of the volume of the esophagus and of the volume of refluxate in the esophagus. For example, because the multi-channel configuration of catheter 500 permits determination of diameters of the esophageal lumen at different levels during a GER, as illustrated in FIG. 14, the reflux volume can also be determined by modeling at least a portion of the lumen as a revolved trapezoidal tank. The small size of the selected transducer elements permitted construction of the prototyped embodiment by attaching the transducers to an MII-pH catheter in the depicted configuration. As compared to the cylindrical model used in the single-element catheter, the multichannel configuration determines diameters from different esophageal levels and thereby enables more accurate GER volume assessment.

Some embodiments of the present systems and methods for multichannel ultrasonic GER volume monitoring include an algorithm including several general components. First, once the system starts, the longitudinal channel (transducers 512*a*, 512*b*) collect ultrasonic data at a certain repetition rate (i.e. 10 Hz). Second, when refluxate is present between the longitudinal sensors, the amount of received ultrasound will increase above a threshold value and thereby indicate a GER episode. During an indicated GER event or episode, the longitudinal channel (transducers 512*a*, 512*b*) and transversal channel (516*a*, 516*b*) collect ultrasonic data to enable the controller (e.g., processor) to determine the diameters on different levels of the esophagus. GER volume at a given time point can then be calculated from the two acquired diameters and the revolved trapezoid model. In some embodiments, the collected and/or determined information can be logged into a non-volatile memory and/or displayed to facilitate review by medical personnel. Because the longitudinal pair is relatively more-sensitive to reflux material than a single longitudinal transducer, GER detection is less affected by other physiological events (e.g., coughing, belching, respiration, etc.). Signal processing in embodiments of the multichannel configuration can therefore be simplified, which may make the multichannel configuration easier to implement in substantially real-time and/or in a clinical setting. Other embodiments of the present catheters include two transverse channels, a first transverse channel (516*a*, 516*b*) disposed as shown, and a second transverse channel disposed closer to (e.g., at or within a distance such as 0.5, 1, 1.5, 2 or more centimeters from) distal end 504.

To validate the functionality of the multichannel ultrasonic systems and methods, a series of in-vitro testing were performed with a prototype of catheter 500. Reflux periods were simulated using the computer-controlled mechanical gastroesophageal model shown above in FIG. 5. Catheter 500 was positioned such that pH-sensor 524 was disposed about 5 cm above lower gripper 212*a* (LES). Different volumes of reflux were then simulated to test catheter 500 and the present multi-channel ultrasonic methods. Lower gripper 212*a* (LES) was left partially open, and the diameter of the esophageal body between the transverse channel (516*a*, 516*b*) and the LES was varied during the testing. A reflux event was defined within the period when the transverse channel (516*a*, 516*b*) was submerged about 1 cm under the simulated refluxate. Then, the volume of the simulated refluxate was measured by directing the refluxate into a syringe through a flexible tube. The multi-channel ultrasonic system and method showed good repeatability and accuracy in detecting simulated reflux events and estimating reflux volume.

Figure 15:
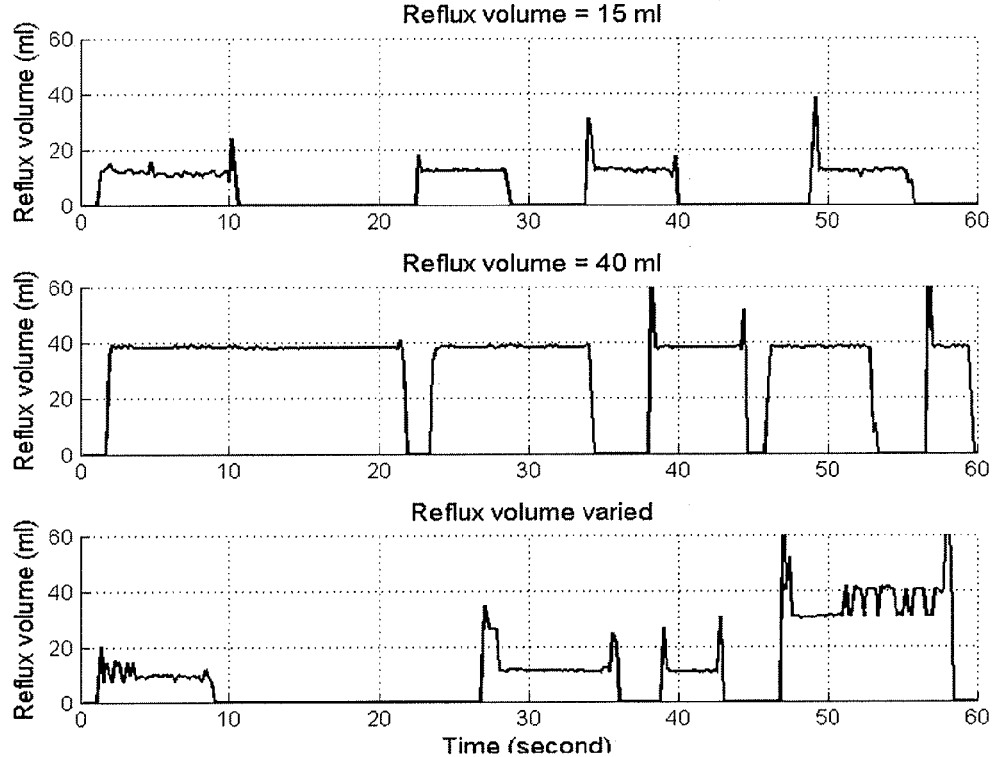
FIG. 15 charts data gathered through tests of the present methods and system including the catheter of FIG. 13A.

FIG. 15 charts the results of three separate experimental trials for testing the volume measurement system and method with the prototype of catheter 500. In the first two trials, volumes of simulated reflux were introduced at 15 ml and 40 ml, respectively. The occurrence of simulated GER were identified clearly and accurately in the real-time ultrasonic data when refluxate was present around the transducers. For the 15 ml reflux episodes, the system output was 11.4±1.0 ml (Mean±Standard Deviation); and for 40 ml reflux episodes, the system output was 38.6±5.4 ml (Mean±Standard Deviation). In the last trial, a variety of reflux volumes were introduced into the gastroesophageal model. The output raw signal of GER volume recording indicates the proposed the system is capable of dynamically distinguishing and determining different GER volumes. Some reflux episodes included sharp spikes at the rising or falling edges, which may be caused by transient acoustic impedance mismatch when ultrasonic transducers were contacted with both liquid and air at the initial or final phase of a GER episode.

While the signals in FIG. 15 raw signals for real-time measurement display, the sharper signal artifacts may be smoothed with simple threshold smoothing methods (e.g., one or more band pass filters and/or smoothing splines, as described above). As such, some embodiments of the present systems (e.g., controllers) and/or methods may include or be configured to filter or smooth the ultrasound signals received from the transducers.

Figure 16:
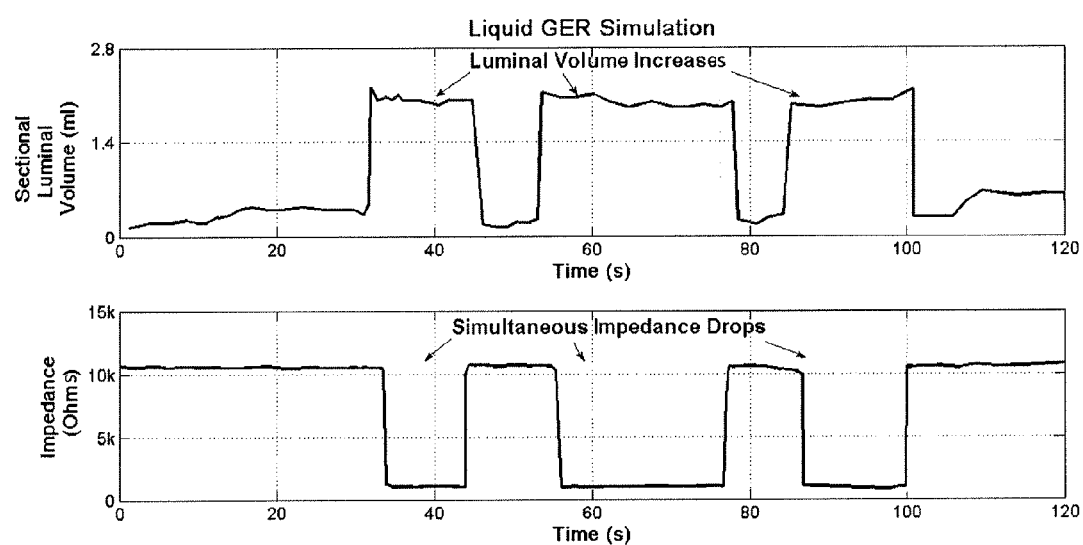
FIG. 16 charts gathered through tests of the present methods and, systems including a catheter similar to that of FIG. 13A with the transverse transceiver pair omitted.
Figure 17:
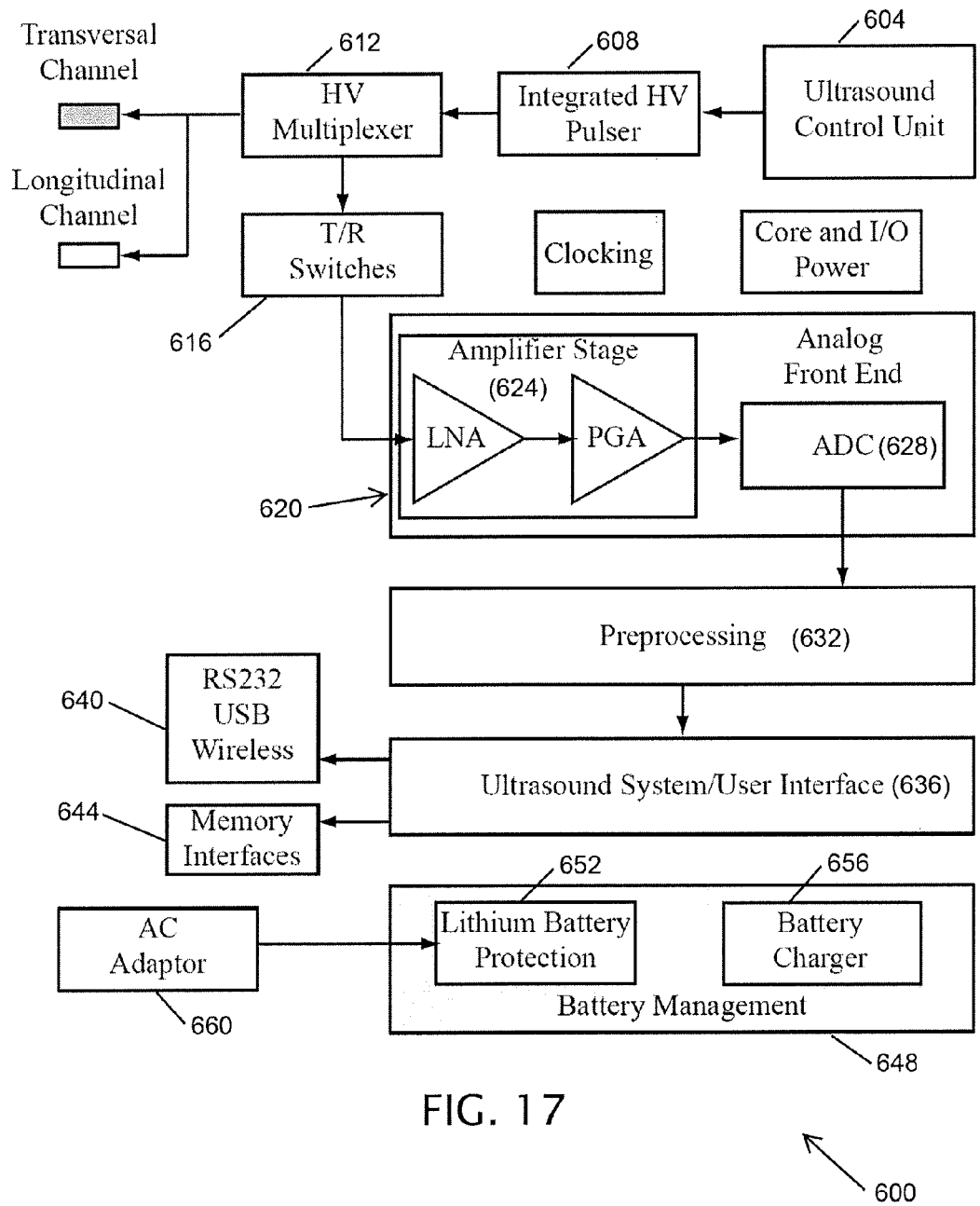
FIG. 17 depicts a block diagram of one embodiment of the present controllers for use with embodiments of the present catheters.

In some embodiments, the transverse ultrasonic channel (transducer pair 516*a*, 516*b*) can be omitted from catheter 500, such that, for example, catheter 500 still includes the longitudinal ultrasonic channel (transducer pair 512*a*, 512*b*). Such embodiments can still be configured to include all functionality other than that resulting from the transverse ultrasonic channel. For illustration, FIG. 16 charts the results of an experimental trial for testing the volume measurement system and method with a prototype of catheter 500 without the transverse ultrasonic channel. The average volume of the simulated GER between the ultrasonic crystals in the silicone-cast model was measured to be 2.4±0.2 ml (n=30) by transferring the simulated refluxates to an external measuring cup. FIG. 16 depicts samples obtained during a 120-second period. It can be observed that 3 GER episodes in total were indicated by increases in the volumetric chart. The results were confirmed by the simultaneous impedance recording charted on the lower portion of FIG. 16. According to the samples of volumetric measurements during repeated simulations (n=30), the average SLV in the vicinity of the ultrasonic probe during GER episodes was 2.0±0.3 ml. It should be noted that there was about 1.5-second time delay in the impedance system comparing to the ultrasonic system during the onset of GER, which was due to the fact that the sensing point of the distal impedance channel was 3 cm above the position of the ultrasonic probe and the rate of change of the top of the refluxate during the simulated GER was approximately 2 cm/s.

FIG. 1 depicts a block diagram of one embodiment of the present controllers 600 configured to be coupled to multi-channel catheter 500 such that controller 600 can receive ultrasonic signals from the longitudinal ultrasonic transducer pair (512*a*, 512*b*), and from the transverse ultrasonic transducer pair (516*a*, 516*b*). In the embodiment shown, controller 600 is further configured to determine from the ultrasonic signals an indication of reflux volume during a gastroesophageal reflux event of a patient, and/or to determine an indication of esophageal volume, as described above. In the embodiment shown, controller 600 includes an ultrasound control unit 604 coupled to a suitable pulse generator or pulser 608 for generating ultrasonic pulses. Ultrasound control unit 604 and pulser 608 are coupled to a multiplexer 612 for interfacing with longitudinal channel (512a, 512b) and transverse channel (516a, 516b). In the embodiment shown, controller 600 further comprises one or more switches 616 coupled to multiplexer 612 and an analog front-end module 620 for receiving ultrasonic signals from the longitudinal and transverse channels. In the embodiment shown, analog front-end module 620 includes an amplifier stage 624 configured to amplify the ultrasonic signals, and an analog-to-digital converter (ADC) 628 to convert the amplified signals to a digital format. Analog front-end module 620 may also include clocking and/or local power components. In the embodiment shown, controller 600 further comprises a processor or other suitable device 632 for preprocessing of the digital signals (e.g., filtering, smoothing, etc.), and a primary processing unit 636 for final processing of the signals (e.g., determination, monitoring, and/or display of processed signal, determined volume, and/or identification of GER events). In some embodiments, processor or other device 632 and primary processing unit 636 combined in a single processor programmed or otherwise configured to perform the preprocessing and final processing functions. In the embodiment shown, primary processing unit 636 includes an output 640, such as, for example, an RS232 and/or USB connection, and/or a wireless interface (e.g., WiFi, Bluetooth, etc.); and/or one or more data loggers or memory interfaces 644 (e.g., flash memory, writable CD or DVD drive, SD card interface, etc.). In some embodiments, controller 600 can include a display and/or user-interface, such as an LCD module, touchscreen, and/or keyboard. In the embodiment shown, controller 600 further includes a battery management module 648 configured to receive one or more batteries, and comprising a backup battery 652 and/or battery charger 656. Module 648 may also be configured to be coupled (e.g., removably) to an AC adaptor 660.

In some embodiments, controller 600 may be configured for 24-hour ambulatory monitoring. For example, controller 600 may be portable (e.g., may be enclosed and/or housed in a self-contained housing and/or may be configured to operate on battery power only for a period of time, such as, for example, at least 1, 2, 3, 4, or more hours without external AC power), and/or may have an overall volume that is equal to, less than, or between, any of: 2000, 300, 200, 150, 100, or less cubic inches. Controller 600 is illustrative of a structure for a controller that can be used with the single-channel longitudinal catheters described above, and need only be simplified to collect data from the single channel and programmed or otherwise configured to process the ultrasonic signals as described above for the single-channel longitudinal catheter.

Some embodiments of the present methods include calibrating the ultrasonic system for a specific patient. Some such methods comprise obtaining and/or recording baseline acoustic properties (e.g., acoustic impedance) of the patient's esophageal tissue by collecting ultrasonic data when there is no refluxate in the patient's esophagus. Some such methods comprise obtaining and/or recording acoustic data during one or more swallowing events in which the patient swallows a known quantity of a known substance (e.g., water). In some embodiments, controller 600 is configured to automatically obtain and/or record baseline acoustic properties of the patient's esophagus and/or to determine the resting or baseline diameter(s) of the patient's esophagus when the catheter is initially intubated and/or at periodic intervals of time thereafter when no reflux liquid is detected in the patient's esophagus.

The various illustrative embodiments of the present devices and kits are not intended to be limited to the particular forms disclosed. Rather, they include all modifications and alternatives falling within the scope of the claims. For example, embodiments other than the one shown may include some or all of the features of the depicted embodiment.

The claims are not intended to include, and should not be interpreted to include, means-plus- or step-plus-function limitations, unless such a limitation is explicitly recited in a given claim using the phrase(s) "means for" or "step for," respectively.

REFERENCES

The following references, to the extent that they provide exemplary procedural or other details supplementary to those set forth herein, are specifically incorporated herein by reference.

[1] United State National Institute of Health, "Digestive disease statistics". [Online]. Available: http://digestive.niddk.nih.gov/statistics/statistics.htm [Oct. 1, 2009].

[2] M. Patti, P. Fisichella, "Chapter 20. Esophagus & Diaphragm," in Current Diagnosis & Treatment: Surgery, 13th ed., Doherty G M. [Online]. Available: http://www.accessmedicine.com/content.aspx?aID=5215311 [Oct. 6, 2009].

[3] A. Klauser, N. Schindlbeck, and S. Muller-Lissner. "Symptom in gastro-oesophageal reflux disease." Lancet, vol. 335, pp. 205-208, January 1990.

[4] N. Shaheen and D. Ransohoff. "Gastroesophageal reflux, barrett esophagus and esophageal cancer: scientific review." Journal of the American Medical Association, vol. 287, pp. 1972-81, April 2002.

[5] S. Spechler. "Clinical practice. Barrett's Esophagus." New England Journal of Medicine, vol. 346, pp. 836-42, March 2002.

[6] D. Sifrim. "Relevance of volume and proximal extent of reflux in gastro-oesophageal reflux disease." Gut, vol. 54, pp. 175-178, July 2005.

[7] N. Tipnis, J. Liu J. Puckett, and R. Mittal. "Common cavity pressure during gastroesophageal reflux: reassessment using simultaneous pressure, impedance, and ultrasound imaging." Am J Physiol Gastrointest Liver Physiol, vol. 290, pp. 1149-56, 2006.

[8] R. Mittal, J. Liu, and J. Puckett. "Sensory and Motor Function of the Esophagus: Lessons from Ultrasound Imaging." Gastroenterology, vol. 128, pp. 487-497, August 2005.

[9] W. Hedrick. Ultrasound physics and instrumentation. St. Louis, Mo.: Elsevier Mosby, 2005, pp. 1-82.

[10] W. Barlow and R. Orlando. "The pathogenesis of heartburn in nonerosive reflux disease: a unifying hypothesis." Gastroenterology, vol. 128, pp. 771-8, August 2005.

[11] D. Sifrim, R. Mittal, R. Fass, et al. "Review article: acidity and volume of the refluxate in the genesis of gastro-oesophageal reflux disease symptoms." Alimentary pharmacology & therapeutics, vol. 25, pp. 1003-1015, 2007.

[12] F. Gonzalez, F. Arguelles, B. Rodriguez, et al. "Gastroesophageal Scintigraphy: A Useful Screening Test for GE Reflux." Journal of Pediatric Gastroenterology and Nutrition, vol. 6, pp. 217-219, 1987.
[13] R. Sellar, J. De Caestecker and R. Heading. "Barium Radiology: A Sensitive Test for Gastro-oesophageal Reflux." Clinical Radiology, vol. 38, pp. 303-307, 1987.
[14] A. Lazarescu and D. Sifrim. "Ambulatory Monitoring of GERD: Current Technology." Gastroenterol Clin N Am, vol. 37, pp. 793-805, 2008.
[15] K. Gwendolyn, D. Robin, B. Vivek, S. Scott, et al, "Chapter 18. Respiratory Tract & Mediastinum," in Current Diagnosis & Treatment: Pediatrics, 19th ed., W. Hay, Jr., M. Levin, J. Sondheimer and R. Deterding. [Online]. Available: http://www.accessmedicine.com/content.aspx?aID=3402130. [Nov. 2, 2009].
[16] J. Silny, "Intraluminal multiple electrical impedance procedure for measurement of gastrointestinal motility," Journal of Gastrointestinal Motility, vol. 3, pp. 151-62, 1991.
[17] H. Imam, S. Shay, A. Ali, et al. "Bolus transit patterns in healthy subjects: a study using simultaneous impedance monitoring, videoesophagram, and esophageal manometry." Am J Physiol Gastrointest Liver Physiol, vol. 288, pp. G1000-1006, 2005.
[18] M. Simren, J. Silny, R. Holloway, et al. "Relevance of ineffective oesophageal motility during oesophageal acid clearance." Gut, vol. 52, pp. 784-790, 2003.
[19] S. Orenstein, H. Magill and P. Brooks. "Thickening of infant feedings for therapy of gastroesophageal reflux." J Pediatr, vol. 110, pp. 181-186, 1987.
[20] J. Pandolfino, G. Shi, B. Trueworthy, et al. "Esophagogastric junction opening during relaxation distinguishes nonhernia reflux patients, hernia patients, and normal subjects." Gastroenterology, vol. 125, pp. 1018-1024, 2003.
[21] R. Srinivasan, M. Vela, P. Katz, et al. "Esophageal function testing using multichannel intraluminal impedance." Am J Physiol Gastrointest Liver Physiol, vol. 280, pp. G457-462, 2001.
[22] W. Yang, T. Fung, K. Chian, et al. "Finite element simulation of food transport through the esophageal body." World J Gastroenterol, vol. 13, pp. 1352-1359, 2007.
[23] L. Johnon, Physiology of the Gastrointestinal Tract. New York: Raven Press, 1987.
[24] GI Motility Online, "Physiology of esophageal motility". [Online]. Available: http://www.nature.com/gimo/contents/pt1/full/gimo3.html [Mar. 20, 2010].
[25] W. Barlow and R. Orlando. "The pathogenesis of heartburn in nonerosive reflux disease: a unifying hypothesis." *Gastroenterology*, vol. 128, pp. 771-8, August 2005.
[26] Y. Yorozu N. Tipnis, J. Liu J. Puckett, and R. Mittal. "Common cavity pressure during gastroesophageal reflux: reassessment using simultaneous pressure, impedance, and ultrasound imaging." *Am J Physiol Gastrointest Live*, vol. 290, pp. 1149-56, 2006.
[27] H. Kuttruff. *Acoustic An introduction*. New York, N.Y.: Taylor & Francis, 2007, pp. 258-282, 345-348.
[28] S. Manoli, W. Lochner, S. Oswald, et al. "Estimation of Ventricular Volume with an Intracardiac Ultrasonic Catheter Catheter," *Pflgers Arch*, vol 349, pp. 369-376, 1974.
[30] U.S. Pat. No. 4,119,498 (Edwall et al.)
[31] U.S. Pat. No. 4,417,583 (Bechai et al.)
[32] U.S. Pat. No. 4,802,490 (Johnston)
[33] U.S. Pat. No. 5,247,938 (Silverstein et al.)
[34] U.S. Pat. No. 5,479,928 (Cathignol et al.)
[35] U.S. Pat. No. 5,524,622 (Wilson)
[36] U.S. Pat. No. 5,833,625 (Essen-Moller)
[37] U.S. Pat. No. 6,398,734 (Cimochowski et al.)
[38] U.S. Patent Application Pub. No. US 2005/0182342 (Dinsmoor et al.)
[39] U.S. Patent No. Application Pub. No. US 2008/0004547 (Dinsmoor et al.)

The invention claimed is:
1. An apparatus comprising:
a catheter having a distal end;
a spaced longitudinal ultrasonic transducer pair coupled to the catheter such that respective faces of the ultrasonic transducers of the longitudinal ultrasonic transducer pair are oriented toward each other when the catheter is straight; and
where the catheter is configured to be coupled to a controller such that the controller can receive ultrasonic signals from the longitudinal ultrasonic transducer pair to identify the presence of reflux material in a patient's esophagus based on a signal received by one of the ultrasonic transducers of the longitudinal ultrasonic transducer pair and transmitted from the other ultrasonic transducer of the longitudinal ultrasonic transducer pair.
2. The apparatus of claim 1, further comprising:
a controller configured to be coupled to the catheter such that the controller can receive signals from the longitudinal ultrasonic transducer pair, the controller further configured to determine from the ultrasonic signals an indication of reflux volume during a gastroesophageal reflux event of a patient.
3. The apparatus of claim 1, further comprising:
a plurality of electrodes coupled in spaced relation along a length of the catheter;
where the catheter is configured to be coupled to a controller such that the controller can receive impedance signals from the plurality of electrodes.
4. The apparatus of claim 3, further comprising:
a pH sensor coupled to the catheter;
where the catheter is further configured to be coupled to a controller such that the controller can receive pH signals from the pH sensor.
5. The apparatus of claim 3, further comprising:
a transverse ultrasonic transducer pair coupled to the catheter;
where the catheter is configured to be coupled to a controller such that the controller can receive ultrasonic signals from the transverse ultrasonic transducer pair.
6. The apparatus of claim 5, further comprising:
a controller configured to be coupled to the catheter such that the controller can receive signals from the longitudinal ultrasonic transducer pair, and from the transverse ultrasonic transducer pair, the controller further configured to determine from the ultrasonic signals an indication of esophageal volume, and an indication of reflux volume during a gastroesophageal reflux event of a patient.
7. The apparatus of claim 6, where the catheter is configured to be disposed within an esophagus of a patient such that the longitudinal ultrasonic transducer pair and the transverse ultrasonic transducer pair are disposed at or a distance above the patient's lower esophageal sphincter (LES), and the controller is configured to determine a first radius of the esophagus based the ultrasonic signals received from the longitudinal transducer pair, and a second radius of the esophagus based on ultrasonic signals received from the transverse transducer pair.

8. The apparatus of claim 7, where the controller is configured to determine an indication of reflux volume by modeling at least a portion of the esophagus as revolved trapezoidal tank having the first radius and the second radius.

9. The apparatus of claim 6, where the controller is configured to filter at least one of the signals received from the ultrasonic transducer pairs, and the indications of reflux volume determined, to remove events having a duration below a threshold duration.

* * * * *